US007569375B2

(12) United States Patent
Stampfer et al.

(10) Patent No.: US 7,569,375 B2
(45) Date of Patent: Aug. 4, 2009

(54) ALCOHOL DEHYDROGENASES WITH INCREASED SOLVENT AND TEMPERATURE STABILITY

(75) Inventors: Wolfgang Stampfer, Steindorf (AT); Birgit Kosjek, Judenburg (AT); Wolfgang Kroutil, Graz (AT); Kurt Faber, Graz (AT); Jürgen Eck, Bensheim (DE); Frank Niehaus, Heppenheim (DE)

(73) Assignee: Codexis, Inc., Redwood City, CA (US)

( * ) Notice: Subject to any disclaimer, the term of this patent is extended or adjusted under 35 U.S.C. 154(b) by 128 days.

(21) Appl. No.: 10/666,205

(22) Filed: Sep. 18, 2003

(65) Prior Publication Data

US 2004/0157305 A1 Aug. 12, 2004

Related U.S. Application Data

(63) Continuation-in-part of application No. PCT/EP03/02439, filed on Mar. 10, 2003.

(30) Foreign Application Priority Data

Mar. 18, 2002 (EP) .................... 02405204

(51) Int. Cl.
*C12N 9/04* (2006.01)
*C12N 15/00* (2006.01)
*C12P 21/04* (2006.01)
*C12N 1/20* (2006.01)
*C12Q 1/00* (2006.01)
*C12Q 1/68* (2006.01)
*C07H 21/04* (2006.01)

(52) U.S. Cl. ............... 435/190; 435/440; 435/69.1; 435/71.1; 435/252.3; 435/320.1; 435/4; 435/6; 536/23.2

(58) Field of Classification Search ............. 435/190, 435/440, 4, 6, 15, 18, 25, 69.1, 71.1, 252.3, 435/320.1; 536/23.2, 23.7
See application file for complete search history.

(56) References Cited

U.S. PATENT DOCUMENTS 6,255,092 B1 7/2001 Kojima et al. .............. 435/190

FOREIGN PATENT DOCUMENTS

WO 03/078615 9/2003

OTHER PUBLICATIONS

Wang et al. Cloning, sequence analysis, and expression in *Escherichia coli* of the gene encoding phenylacetaldehyde reductase from styrene-assimilating Corynebacterium sp. strain ST-10. Appl Microbiol Biotechnol. Sep. 1999;52(3):386-92.*
Wang et al.—Sequence Alignment.*
Stampfer et al. Online Publication Date.*

B. Kosjek et al., Biotechnology and Bioengineering, vol. 86, No. 1, Apr. 5, 2004, pp. 55-62.
Database Accession No. AJ491307, Jun. 24, 2002, "Rhodococcus ruber padh gene (partial), sadh gene And sudh gene", Secondary Alcohol Dehydrogenase Q8KLT9, Abstract.
W. A. van der Donk et al., Current Opinion in Biotechnology, vol. 14, (2003), pp. 421-426.
N. Itoh et al., Eur. J. Biochem., vol. 269, (2002), pp. 2394-2402.
W. Stampfer et al., J. Org. Chem. vol. 68, (2003), pp. 402-406.
W. Stampfer et al., Biotechnology and Bioengineering, vol. 81, No. 7, Mar. 30, 2003, pp. 865-869.
W. Stampfer et al., Angew. Chem. Int. Ed. vol. 41, No. 6, (2002) pp. 1014-1017.
M. Reid et al., Critical Reviews in Microbiology, vol. 20, (1), pp. 13-56, (1994).
P. Schenkels et al., Microbiology, vol. 146, (2000), pp. 775-785.
M. Pogorevc et al., Tetrahedron: Asymmetry, vol. 13, (2002), pp. 1435-1441.
T.-K. Kim et al., J. Microbiol. Biotechnol. vol. 12, (1), (2002), pp. 39-45.
K. Kostichka et al., Journal of Bacteriology, vol. 183, No. 21, Nov. 2001, pp. 6478-6486.
T. Hirata et al., Phytochemistry, vol. 55, (2000), pp. 297-303.
K. Nakamura et al., J. Org. Chem., vol. 63, (1998), pp. 8957-8964.
A. Goswami et al., Tetrahedron: Asymmetry, vol. 11, (2000), pp. 3701-3709.
K. Nakamura et al., J. Chem. Soc., Perkin Trans. I, (1999), pp. 2397-2402.
G. Fantin et al., Tetrahedron: Asymmetry, vol. 11, (2000), pp. 2367-2373.
W. Hummel et al., Ann. N.Y. Acad. Sci., vol. 799, (1996), pp. 713-716.
W. Hummel, Adv. Biochem. Eng./Biotechnol., vol. 58, (1997), pp. 145-184.
E. Breysse et al., Tetrahedron: Asymmetry, vol. 9, (1998), pp. 897-900.
F. Touchard et al., Journal of Organometallic Chemistry, vol. 567, (1998), pp. 133-136.
T. Ooi et al., Tetrahedron Letters, vol. 40, (1999), pp. 2137-2138.
K. Akamanchi et al., Tetrahedron Letters, vol. 38, No. 39, pp. 6925-6928, (1997).
C. F. de Graauw et al., Synthesis, (1994), pp. 1007-1017.

* cited by examiner

*Primary Examiner*—Yong D Pak
(74) *Attorney, Agent, or Firm*—Christie, Parker & Hale, LLP.

(57) ABSTRACT

The invention relates to biocatalysts showing alcohol dehydrogenase activity obtainable from *Rhodococcus ruber*, their preparation, their use in the oxidation of secondary alcohols and/or the reduction of ketones, as well as nucleic acids coding for these alcohol dehydrogenases and microorganisms transformed with nucleic acids coding for these biocatalysts and their use for producing the biocatalyst or oxidizing secondary alcohols and/or reducing ketones.

2 Claims, 2 Drawing Sheets

SEQUENCE LISTING

```
<160> NUMBER OF SEQ ID NOS: 51

<210> SEQ ID NO 1
<211> LENGTH: 8
<212> TYPE: PRT
<213> ORGANISM: Rhodococcus ruber DSM 14855

<400> SEQUENCE: 1

Glu Val Gly Asp Ala Ala Ala Arg
1               5

<210> SEQ ID NO 2
<211> LENGTH: 11
<212> TYPE: PRT
<213> ORGANISM: Rhodococcus ruber DSM 14855
<220> FEATURE:
<221> NAME/KEY: MISC_FEATURE
<222> LOCATION: (3)..(3)
```

-continued

```
<223> OTHER INFORMATION: X in position 3 is either leucine or isoleucine
<220> FEATURE:
<221> NAME/KEY: MISC_FEATURE
<222> LOCATION: (9)..(9)
<223> OTHER INFORMATION: X in position 9 is either leucine or isoleucine

<400> SEQUENCE: 2

Thr Asp Xaa Phe Glu Val Val Ala Xaa Ala Arg
1               5                   10

<210> SEQ ID NO 3
<211> LENGTH: 10
<212> TYPE: PRT
<213> ORGANISM: Rhodococcus ruber DSM 14855
<220> FEATURE:
<221> NAME/KEY: MISC_FEATURE
<222> LOCATION: (9)..(9)
<223> OTHER INFORMATION: X in position 3 is either leucine or isoleucine

<400> SEQUENCE: 3

Ser Gly Ala Gly Ala Ala Asp Ala Xaa Arg
1               5                   10

<210> SEQ ID NO 4
<211> LENGTH: 10
<212> TYPE: PRT
<213> ORGANISM: Rhodococcus ruber DSM 14855
<220> FEATURE:
<221> NAME/KEY: MISC_FEATURE
<222> LOCATION: (2)..(2)
<223> OTHER INFORMATION: X in position 2 is either leucine or isoleucine
<220> FEATURE:
<221> NAME/KEY: MISC_FEATURE
<222> LOCATION: (6)..(6)
<223> OTHER INFORMATION: X in position 6 is either leucine or isoleucine

<400> SEQUENCE: 4

Val Xaa Ala Val Asp Xaa Asp Asp Asp Glu
1               5                   10

<210> SEQ ID NO 5
<211> LENGTH: 12
<212> TYPE: PRT
<213> ORGANISM: Rhodococcus ruber DSM 14855
<220> FEATURE:
<221> NAME/KEY: MISC_FEATURE
<222> LOCATION: (2)..(2)
<223> OTHER INFORMATION: X in position 2 is either leucine or isoleucine
<220> FEATURE:
<221> NAME/KEY: MISC_FEATURE
<222> LOCATION: (6)..(6)
<223> OTHER INFORMATION: X in position 6 is either leucine or isoleucine
<220> FEATURE:
<221> NAME/KEY: MISC_FEATURE
<222> LOCATION: (10)..(10)
<223> OTHER INFORMATION: X in position 10 is either leucine or
      isoleucine
<220> FEATURE:
<221> NAME/KEY: MISC_FEATURE
<222> LOCATION: (10)..(10)
<223> OTHER INFORMATION: X in position 10 is an unidentified amino acid
<220> FEATURE:
<221> NAME/KEY: MISC_FEATURE
<222> LOCATION: (12)..(12)
<223> OTHER INFORMATION: X in position 12 is an unidentified amino acid

<400> SEQUENCE: 5

Val Xaa Ala Val Asp Xaa Asp Asp Asp Xaa Arg Xaa
1               5                   10

<210> SEQ ID NO 6
```

<211> LENGTH: 11
<212> TYPE: PRT
<213> ORGANISM: Rhodococcus ruber DSM 14855
<220> FEATURE:
<221> NAME/KEY: MISC_FEATURE
<222> LOCATION: (1)..(2)
<223> OTHER INFORMATION: XX in position 1,2 is either one of the
      sequences Thr-Asp or Asp-Thr
<220> FEATURE:
<221> NAME/KEY: MISC_FEATURE
<222> LOCATION: (3)..(3)
<223> OTHER INFORMATION: X in position 3 is either leucine or isoleucine
<220> FEATURE:
<221> NAME/KEY: MISC_FEATURE
<222> LOCATION: (9)..(9)
<223> OTHER INFORMATION: X in position 9 is either leucine or isoleucine

<400> SEQUENCE: 6

Xaa Xaa Xaa Met Glu Val Val Ala Xaa Ala Arg
1               5                   10

<210> SEQ ID NO 7
<211> LENGTH: 22
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: misc_feature
<222> LOCATION: (14)..(14)
<223> OTHER INFORMATION: n is a, g, c or t
<220> FEATURE:
<221> NAME/KEY: misc_feature
<222> LOCATION: (17)..(17)
<223> OTHER INFORMATION: n is a, g, c or t

<400> SEQUENCE: 7
cggagccggg cccnggnsar rt                                               22

<210> SEQ ID NO 8
<211> LENGTH: 27
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: misc_feature
<222> LOCATION: (19)..(19)
<223> OTHER INFORMATION: n is a, g, c or t
<220> FEATURE:
<221> NAME/KEY: misc_feature
<222> LOCATION: (22)..(22)
<223> OTHER INFORMATION: n is a, g, c or t
<220> FEATURE:
<221> NAME/KEY: misc_feature
<222> LOCATION: (25)..(25)
<223> OTHER INFORMATION: n is a, g, c or t

<400> SEQUENCE: 8
ctacgagctg ccgctgacny tnggnca                                          27

<210> SEQ ID NO 9
<211> LENGTH: 26
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene

```
<220> FEATURE:
<221> NAME/KEY: misc_feature
<222> LOCATION: (18)..(18)
<223> OTHER INFORMATION: n is a, g, c or t
<220> FEATURE:
<221> NAME/KEY: misc_feature
<222> LOCATION: (24)..(24)
<223> OTHER INFORMATION: n is a, g, c or t

<400> SEQUENCE: 9
gtcgtcgtct acggcccntg gggntg                                              26

<210> SEQ ID NO 10
<211> LENGTH: 29
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: misc_feature
<222> LOCATION: (21)..(21)
<223> OTHER INFORMATION: n is a, g, c or t
<220> FEATURE:
<221> NAME/KEY: misc_feature
<222> LOCATION: (24)..(24)
<223> OTHER INFORMATION: n is a, g, c or t

<400> SEQUENCE: 10
gacaacgtcg tcgtctacgg nccntgggg                                           29

<210> SEQ ID NO 11
<211> LENGTH: 24
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: misc_feature
<222> LOCATION: (14)..(14)
<223> OTHER INFORMATION: n is a, g, c or t
<220> FEATURE:
<221> NAME/KEY: misc_feature
<222> LOCATION: (17)..(17)
<223> OTHER INFORMATION: n is a, g, c or t
<220> FEATURE:
<221> NAME/KEY: misc_feature
<222> LOCATION: (23)..(23)
<223> OTHER INFORMATION: n is a, g, c or t

<400> SEQUENCE: 11
gcaccggcgg cctnggncay gtng                                                24

<210> SEQ ID NO 12
<211> LENGTH: 25
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: misc_feature
<222> LOCATION: (20)..(20)
<223> OTHER INFORMATION: n is a, g, c or t
<220> FEATURE:
<221> NAME/KEY: misc_feature
<222> LOCATION: (23)..(23)
<223> OTHER INFORMATION: n is a, g, c or t
```

<400> SEQUENCE: 12
gctggtcgcc gacgaartcn arnac					25

<210> SEQ ID NO 13
<211> LENGTH: 27
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: misc_feature
<222> LOCATION: (19)..(19)
<223> OTHER INFORMATION: n is a, g, c or t

<400> SEQUENCE: 13
catcagctcg gtgcggshnc cccarta					27

<210> SEQ ID NO 14
<211> LENGTH: 26
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: misc_feature
<222> LOCATION: (18)..(18)
<223> OTHER INFORMATION: n is a, g, c or t
<220> FEATURE:
<221> NAME/KEY: misc_feature
<222> LOCATION: (21)..(21)
OTHER INFORMATION: n is a, g, c or t

<400> SEQUENCE: 14
gccaggtcga cgacctcnrt narytc					26

<210> SEQ ID NO 15
<211> LENGTH: 26
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: misc_feature
<222> LOCATION: (3)..(3)
<223> OTHER INFORMATION: n is a, g, c or t
<220> FEATURE:
<221> NAME/KEY: misc_feature
<222> LOCATION: (12)..(12)
<223> OTHER INFORMATION: n is a, g, c or t
<220> FEATURE:
<221> NAME/KEY: misc_feature
<222> LOCATION: (18)..(18)
<223> OTHER INFORMATION: n is a, g, c or t
<220> FEATURE:
<221> NAME/KEY: misc_feature
<222> LOCATION: (19)..(19)
<223> OTHER INFORMATION: n is a, g, c or t
<220> FEATURE:
<221> NAME/KEY: misc_feature
<222> LOCATION: (20)..(20)
<223> OTHER INFORMATION: n is a, g, c or t
<220> FEATURE:
<221> NAME/KEY: misc_feature
<222> LOCATION: (21)..(21)
<223> OTHER INFORMATION: n is a, g, c or t

<400> SEQUENCE: 15

```
ggncacgarg gngtcggnnn ngtcgc                                          26
```

<210> SEQ ID NO 16
<211> LENGTH: 17
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: misc_feature
<222> LOCATION: (3)..(3)
<223> OTHER INFORMATION: n is a, g, c or t
<220> FEATURE:
<221> NAME/KEY: misc_feature
<222> LOCATION: (12)..(12)
<223> OTHER INFORMATION: n is a, g, c or t

<400> SEQUENCE: 16

```
ggncacgarg gngtcgg                                                    17
```

<210> SEQ ID NO 17
<211> LENGTH: 17
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: modified_base
<222> LOCATION: (6)..(6)
<223> OTHER INFORMATION: n here stands for inosine
<220> FEATURE:
<221> NAME/KEY: misc_feature
<222> LOCATION: (3)..(3)
<223> OTHER INFORMATION: n is a, g, c or t
<220> FEATURE:
<221> NAME/KEY: misc_feature
<222> LOCATION: (6)..(6)
<223> OTHER INFORMATION: n is here inosine
<220> FEATURE:
<221> NAME/KEY: modified_base
<222> LOCATION: (9)..(9)
<223> OTHER INFORMATION: n is here inosine
<220> FEATURE:
<221> NAME/KEY: misc_feature
<222> LOCATION: (9)..(9)
<223> OTHER INFORMATION: n is here inosine
<220> FEATURE:
<221> NAME/KEY: modified_base
<222> LOCATION: (12)..(12)
<223> OTHER INFORMATION: n is here inosine
<220> FEATURE:
<221> NAME/KEY: misc_feature
<222> LOCATION: (12)..(12)
<223> OTHER INFORMATION: n is here inosine
<220> FEATURE:
<221> NAME/KEY: modified_base
<222> LOCATION: (15)..(15)
<223> OTHER INFORMATION: n is here inosine
<220> FEATURE:
<221> NAME/KEY: misc_feature
<222> LOCATION: (15)..(15)
<223> OTHER INFORMATION: n here stands for inosine

<400> SEQUENCE: 17

```
ccnytnacny tnggnca                                                    17
```

<210> SEQ ID NO 18
<211> LENGTH: 17
<212> TYPE: DNA

```
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: modified_base
<222> LOCATION: (9)..(9)
<223> OTHER INFORMATION: in each case i stands for inosine
<220> FEATURE:
<221> NAME/KEY: misc_feature
<222> LOCATION: (9)..(9)
<223> OTHER INFORMATION: n here stands for inosine
<220> FEATURE:
<221> NAME/KEY: misc_feature
<222> LOCATION: (3)..(3)
<223> OTHER INFORMATION: n is a, g, c or t
<220> FEATURE:
<221> NAME/KEY: modified_base
<222> LOCATION: (12)..(12)
<223> OTHER INFORMATION: n here stands for inosine
<220> FEATURE:
<221> NAME/KEY: misc_feature
<222> LOCATION: (12)..(12)
<223> OTHER INFORMATION: n here stands for inosine

<400> SEQUENCE: 18
gtntayggnc cntgggg                                                  17

<210> SEQ ID NO 19
<211> LENGTH: 17
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: modified_base
<222> LOCATION: (9)..(9)
<223> OTHER INFORMATION: n stands for inosine
<220> FEATURE:
<221> NAME/KEY: misc_feature
<222> LOCATION: (9)..(9)
<223> OTHER INFORMATION: n here stands for inosine
<220> FEATURE:
<221> NAME/KEY: modified_base
<222> LOCATION: (15)..(15)
<223> OTHER INFORMATION: n here stands for inosine
<220> FEATURE:
<221> NAME/KEY: misc_feature
<222> LOCATION: (15)..(15)
<223> OTHER INFORMATION: n here stands for inosine
<220> FEATURE:
<221> NAME/KEY: misc_feature
<222> LOCATION: (3)..(3)
<223> OTHER INFORMATION: n is a, g, c or t
<220> FEATURE:
<221> NAME/KEY: misc_feature
<222> LOCATION: (6)..(6)
<223> OTHER INFORMATION: n is a, g, c or t

<400> SEQUENCE: 19
ccnytnacng aygcngg                                                  17

<210> SEQ ID NO 20
<211> LENGTH: 17
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: modified_base
```

<222> LOCATION: (9)..(9)
<223> OTHER INFORMATION: n here stands for inosine
<220> FEATURE:
<221> NAME/KEY: misc_feature
<222> LOCATION: (9)..(9)
<223> OTHER INFORMATION: n here stands for inosine
<220> FEATURE:
<221> NAME/KEY: modified_base
<222> LOCATION: (12)..(12)
<223> OTHER INFORMATION: n here stands for inosine
<220> FEATURE:
<221> NAME/KEY: misc_feature
<222> LOCATION: (12)..(12)
<223> OTHER INFORMATION: n here stands for inosine
<220> FEATURE:
<221> NAME/KEY: modified_base
<222> LOCATION: (15)..(15)
<223> OTHER INFORMATION: n here stands for inosine
<220> FEATURE:
<221> NAME/KEY: misc_feature
<222> LOCATION: (15)..(15)
<223> OTHER INFORMATION: n here stands for inosine
<220> FEATURE:
<221> NAME/KEY: misc_feature
<222> LOCATION: (3)..(3)
<223> OTHER INFORMATION: n is a, g, c or t

<400> SEQUENCE: 20
ccngcrtcng tnarngg                                                17

<210> SEQ ID NO 21
<211> LENGTH: 17
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: modified_base
<222> LOCATION: (15)..(15)
<223> OTHER INFORMATION: n here stands for inosine
<220> FEATURE:
<221> NAME/KEY: misc_feature
<222> LOCATION: (15)..(15)
<223> OTHER INFORMATION: n here stands for inosine
<220> FEATURE:
<221> NAME/KEY: misc_feature
<222> LOCATION: (3)..(3)
<223> OTHER INFORMATION: n is a, g, c or t
<220> FEATURE:
<221> NAME/KEY: misc_feature
<222> LOCATION: (6)..(6)
<223> OTHER INFORMATION: n is a, g, c or t

<400> SEQUENCE: 21
cgngtncccc artangg                                                17

<210> SEQ ID NO 22
<211> LENGTH: 22
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene

<400> SEQUENCE: 22
atgaaagccc tccagtacac cg                                          22

<210> SEQ ID NO 23
<211> LENGTH: 21
<212> TYPE: DNA

```
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene

<400> SEQUENCE: 23
atgaargcsc tscartacac s                                              21

<210> SEQ ID NO 24
<211> LENGTH: 19
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene

<400> SEQUENCE: 24
tcagcccggg acgaccacc                                                 19

<210> SEQ ID NO 25
<211> LENGTH: 19
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: misc_feature
<222> LOCATION: (2)..(17)
<223> OTHER INFORMATION: in each case n is, independently of the others,
      a, g, c or t

<400> SEQUENCE: 25
anccnggnac nacnacncc                                                 19

<210> SEQ ID NO 26
<211> LENGTH: 27
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: misc_feature
<222> LOCATION: (9)..(9)
<223> OTHER INFORMATION: n is a, g, c or t

<400> SEQUENCE: 26
gtsatcgcng tcgayctsga cgacgac                                        27

<210> SEQ ID NO 27
<211> LENGTH: 26
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: misc_feature
<222> LOCATION: (16)..(18)
<223> OTHER INFORMATION: in each case, n is independently of the other
      a, g, c or t

<400> SEQUENCE: 27
gtcathgcsg tcgacntnga cgacga                                         26
```

<210> SEQ ID NO 28
<211> LENGTH: 20
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: modified_base
<222> LOCATION: (12)..(12)
<223> OTHER INFORMATION: n here stands for inosine
<220> FEATURE:
<221> NAME/KEY: misc_feature
<222> LOCATION: (12)..(12)
<223> OTHER INFORMATION: n here stands for inosine
<220> FEATURE:
<221> NAME/KEY: misc_feature
<222> LOCATION: (3)..(6)
<223> OTHER INFORMATION: n is in each case independently from the other
      a, g, c or t

<400> SEQUENCE: 28
gcngtngayy tngaygayga                                           20

<210> SEQ ID NO 29
<211> LENGTH: 20
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene

<400> SEQUENCE: 29
gtcgatctcg acgacgaccg                                           20

<210> SEQ ID NO 30
<211> LENGTH: 27
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: misc_feature
<222> LOCATION: (19)..(19)
<223> OTHER INFORMATION: n is a, g, c or t

<400> SEQUENCE: 30
gtcgtcgtcs agrtcgacng cgatsac                                   27

<210> SEQ ID NO 31
<211> LENGTH: 26
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: misc_feature
<222> LOCATION: (9)..(11)
<223> OTHER INFORMATION: n in each case is independently from the other
      a, g, c or t

<400> SEQUENCE: 31
tcgtcgtcna ngtcgacsgc datgac                                    26

```
<210> SEQ ID NO 32
<211> LENGTH: 20
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: modified_base
<222> LOCATION: (9)..(18)
<223> OTHER INFORMATION: here n in each case stands for inosine
<220> FEATURE:
<221> NAME/KEY: misc_feature
<222> LOCATION: (9)..(18)
<223> OTHER INFORMATION: n here in each case stands for inosine

<400> SEQUENCE: 32
tcrtcrtcna nrtcnacngc                                           20

<210> SEQ ID NO 33
<211> LENGTH: 19
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene

<400> SEQUENCE: 33
cgtcgtcgag atcgacggc                                            19

<210> SEQ ID NO 34
<211> LENGTH: 21
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: misc_feature
<222> LOCATION: (6)..(6)
<223> OTHER INFORMATION: n is a, g, c or t

<400> SEQUENCE: 34
gargtnggcg csgacgcsgc s                                         21

<210> SEQ ID NO 35
<211> LENGTH: 24
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: misc_feature
<222> LOCATION: (3)..(9)
<223> OTHER INFORMATION: n in each case is independently from the other
      a, g, c or t

<400> SEQUENCE: 35
ggngcsggng csgcsgacgc satc                                      24

<210> SEQ ID NO 36
<211> LENGTH: 20
<212> TYPE: DNA
<213> ORGANISM: Artificial Sequence
<220> FEATURE:
```

<223> OTHER INFORMATION: Sequence used as potential probe for
      identifying Rhodococcus ruber DSM 14855 alcohol dehydrogenase
      A gene
<220> FEATURE:
<221> NAME/KEY: misc_feature
<222> LOCATION: (6)..(18)
<223> OTHER INFORMATION: n is in each case independent from the others
      a, g, c or t

<400> SEQUENCE: 36
gargtnggng cngaygcngc                                                  20

<210> SEQ ID NO 37
<211> LENGTH: 20
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: misc_feature
<222> LOCATION: (15)..(15)
<223> OTHER INFORMATION: n is a, g, c or t

<400> SEQUENCE: 37
gcsgcgtcsg cgccnacrtc                                                  20

<210> SEQ ID NO 38
<211> LENGTH: 20
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: misc_feature
<222> LOCATION: (3)..(15)
<223> OTHER INFORMATION: n is in each case independently from the others
      a, g, c or t

<400> SEQUENCE: 38
gcngcrtcng cnccnacytc                                                  20

<210> SEQ ID NO 39
<211> LENGTH: 24
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: misc_feature
<222> LOCATION: (16)..(22)
<223> OTHER INFORMATION: n is in each case independently from the other
      a, g, c or t

<400> SEQUENCE: 39
gatsgcgtcs gcsgcnccsg cngg                                             24

<210> SEQ ID NO 40
<211> LENGTH: 23
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene

```
<400> SEQUENCE: 40
cgsgcsaggt csacsacgtc cat                                           23

<210> SEQ ID NO 41
<211> LENGTH: 20
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: misc_feature
<222> LOCATION: (3)..(15)
<223> OTHER INFORMATION: n is in each case, independently from the
      others, a, g, c or t

<400> SEQUENCE: 41
ggngcnggng cngcngaygc                                               20

<210> SEQ ID NO 42
<211> LENGTH: 20
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: misc_feature
<222> LOCATION: (6)..(18)
<223> OTHER INFORMATION: n is in each case independently from the others
      a, g, c or t

<400> SEQUENCE: 42
gcrtcngcng cnccngcncc                                               20

<210> SEQ ID NO 43
<211> LENGTH: 14
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene

<400> SEQUENCE: 43
gccgccccgg cgcc                                                     14

<210> SEQ ID NO 44
<211> LENGTH: 17
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene
<220> FEATURE:
<221> NAME/KEY: modified_base
<222> LOCATION: (9)..(15)
<223> OTHER INFORMATION: n here in each case stands for inosine
<220> FEATURE:
<221> NAME/KEY: misc_feature
<222> LOCATION: (9)..(15)
<223> OTHER INFORMATION: n here in each case stands for inosine
<220> FEATURE:
<221> NAME/KEY: misc_feature
<222> LOCATION: (3)..(6)
<223> OTHER INFORMATION: n in each case independently from the other
      stands for a, g, c or t
```

<400> SEQUENCE: 44
ckngcnarng cnacnac                                                    17

<210> SEQ ID NO 45
<211> LENGTH: 26
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene

<400> SEQUENCE: 45
cctgcgcgcg cggccgggag aactac                                          26

<210> SEQ ID NO 46
<211> LENGTH: 27
<212> TYPE: DNA
<213> ORGANISM: Artificial Sequence
<220> FEATURE:
<223> OTHER INFORMATION: Sequence used as potential probe for
      identifying Rhodococcus ruber DSM 14855 alcohol dehydrogenase
      A gene

<400> SEQUENCE: 46
caggatctgg atgccgacgt ggccgag                                         27

<210> SEQ ID NO 47
<211> LENGTH: 1038
<212> TYPE: DNA
<213> ORGANISM: Rhodococcus ruber DSM 14855

<400> SEQUENCE: 47
atgaaagccg tccagtacac cgagatcggc tccgagccgg tcgttgtcga catccccacc      60
ccgacgcccg gccgggtga gatcctgctg aaggtcaccg cggccgggct gtgccactcg      120
gacatcttcg tgatggacat gccggcggcg cagtacgcct acggcctgcc gctcaccctc     180
ggccacgagg gtgtcggcac cgtcgccgaa ctcggcgagg cgtcacggg attcggggtg      240 ggggacgccg tcgccgtgta cgggccgtgg ggctgcggtg cgtgccacgc ctgcgcgcgc     300
ggccgggaga actactgcac ccgcgccgcc gacctgggca tcacgccacc cggtctcggc     360
tcgcccggat cgatggccga gtacatgatc gtcgattcgg cgcgccacct cgtcccgatc     420
ggagacctcg acccggtcgc cgcggcgccc ctcaccgacg ccggtctgac gccgtaccac     480
gcgatctccc gggtcctgcc gctgctgggg ccgggctcga cggccgtcgt catcggtgtc     540
ggcgggctcg gccacgtcgg catccagatc ctgcgcgccg tcagcgcggc ccgtgtgatc     600
gccgtcgacc tcgacgacga ccgtctcgcc ctcgcccgcg aggtcggcgc cgacgcggcg     660
gtgaagtcgg cgccggtgc ggcggacgcg atccgggaac tgaccggcgg ccagggcgcg     720
acggcggtgt cgacttcgt cggcgcccag tcgacgatcg acacggcgca gcaggtggtc     780
gcggtcgacg ggcacatctc ggtcgtgggc atccacgccg gcgcacacgc caaggtcggg     840
ttcttcatga tcccgttcgg cgcctccgtc gtgaccccgt actggggcac ccggtcggaa     900
ctgatggagg tcgtcgcgct ggcccgcgcc ggccggctgg acatccacac cgagacgttc     960
accctcgacg aggggccggc ggcgtaccgg cggctgcgcg agggcagcat ccgcggccgc    1020
ggcgtggtgg ttccctga                                                 1038

<210> SEQ ID NO 48
<211> LENGTH: 345

```
<212> TYPE: PRT
<213> ORGANISM: Rhodococcus ruber DSM 14855

<400> SEQUENCE: 48

Met Lys Ala Val Gln Tyr Thr Glu Ile Gly Ser Glu Pro Val Val
 1               5                  10                  15

Asp Ile Pro Thr Pro Thr Pro Gly Pro Gly Glu Ile Leu Leu Lys Val
             20                  25                  30

Thr Ala Ala Gly Leu Cys His Ser Asp Ile Phe Val Met Asp Met Pro
         35                  40                  45

Ala Ala Gln Tyr Ala Tyr Gly Leu Pro Leu Thr Leu Gly His Glu Gly
     50                  55                  60

Val Gly Thr Val Ala Glu Leu Gly Glu Gly Val Thr Gly Phe Gly Val
 65                  70                  75                  80

Gly Asp Ala Val Ala Val Tyr Gly Pro Trp Gly Cys Gly Ala Cys His
                 85                  90                  95

Ala Cys Ala Arg Gly Arg Glu Asn Tyr Cys Thr Arg Ala Ala Asp Leu
            100                 105                 110

Gly Ile Thr Pro Pro Gly Leu Gly Ser Pro Gly Ser Met Ala Glu Tyr
        115                 120                 125

Met Ile Val Asp Ser Ala Arg His Leu Val Pro Ile Gly Asp Leu Asp
130                 135                 140

Pro Val Ala Ala Ala Pro Leu Thr Asp Ala Gly Leu Thr Pro Tyr His
145                 150                 155                 160

Ala Ile Ser Arg Val Leu Pro Leu Leu Gly Pro Gly Ser Thr Ala Val
                165                 170                 175

Val Ile Gly Val Gly Gly Leu Gly His Val Gly Ile Gln Ile Leu Arg
            180                 185                 190

Ala Val Ser Ala Ala Arg Val Ile Ala Val Asp Leu Asp Asp Asp Arg
        195                 200                 205

Leu Ala Leu Ala Arg Glu Val Gly Ala Asp Ala Ala Val Lys Ser Gly
    210                 215                 220

Ala Gly Ala Ala Asp Ala Ile Arg Glu Leu Thr Gly Gly Gln Gly Ala
225                 230                 235                 240

Thr Ala Val Phe Asp Phe Val Gly Ala Gln Ser Thr Ile Asp Thr Ala
                245                 250                 255

Gln Gln Val Val Ala Val Asp Gly His Ile Ser Val Val Gly Ile His
            260                 265                 270

Ala Gly Ala His Ala Lys Val Gly Phe Phe Met Ile Pro Phe Gly Ala
        275                 280                 285

Ser Val Val Thr Pro Tyr Trp Gly Thr Arg Ser Glu Leu Met Glu Val
    290                 295                 300

Val Ala Leu Ala Arg Ala Gly Arg Leu Asp Ile His Thr Glu Thr Phe
305                 310                 315                 320

Thr Leu Asp Glu Gly Pro Ala Ala Tyr Arg Arg Leu Arg Glu Gly Ser
                325                 330                 335

Ile Arg Gly Arg Gly Val Val Val Pro
            340                 345

<210> SEQ ID NO 49
<211> LENGTH: 10
<212> TYPE: PRT
<213> ORGANISM: Rhodococcus ruber
<220> FEATURE:
<221> NAME/KEY: MISC_FEATURE
<222> LOCATION: (2)..(2)
```

```
<223> OTHER INFORMATION: Xaa is leucine or isoleucine
<220> FEATURE:
<221> NAME/KEY: MISC_FEATURE
<222> LOCATION: (6)..(6)
<223> OTHER INFORMATION: Xaa is leucine or isoleucine

<400> SEQUENCE: 49

Val Xaa Ala Val Asp Xaa Asp Asp Arg
1               5                   10

<210> SEQ ID NO 50
<211> LENGTH: 19
<212> TYPE: PRT
<213> ORGANISM: Rhodococcus ruber
<220> FEATURE:
<221> NAME/KEY: MISC_FEATURE
<222> LOCATION: (18)..(18)
<223> OTHER INFORMATION: Xaa is leucine or isoleucine

<400> SEQUENCE: 50

Glu Val Gly Ala Asp Ala Ala Val Lys Ser Gly Ala Gly Ala Ala Gly
1               5                   10                  15

Ala Xaa Arg

<210> SEQ ID NO 51
<211> LENGTH: 9
<212> TYPE: PRT
<213> ORGANISM: Rhodococcus ruber
<220> FEATURE:
<221> NAME/KEY: MISC_FEATURE
<222> LOCATION: (1)..(1)
<223> OTHER INFORMATION: Xaa is leucine or isoleucine
<220> FEATURE:
<221> NAME/KEY: MISC_FEATURE
<222> LOCATION: (7)..(7)
<223> OTHER INFORMATION: Xaa is leucine or isoleucine

<400> SEQUENCE: 51

Xaa Phe Glu Val Val Ala Xaa Ala Arg
1               5
```

ALCOHOL DEHYDROGENASES WITH INCREASED SOLVENT AND TEMPERATURE STABILITY

This is a continuation in part application based on PCT application No. PCT/EP03/02439 filed Mar. 10, 2003.

SUMMARY OF THE INVENTION

The invention relates to biocatalysts showing alcohol dehydrogenase activity, their preparation, their use in the oxidation of secondary alcohols and/or the reduction of ketones, as well as nucleic acids coding for these alcohol dehydogenases and microorganisms transformed with nucleic acids coding for these biocatalysts and their use for producing the biocatalyst.

BACKGROUND OF THE INVENTION

The Oppenauer oxidation (Op-Ox) and the inverse reduction, the Meerwein-Pondorf-Verley reduction (MPV-Red), are well-established oxidation or reduction processes for alcohols or ketones, respectively. The reactions are possible without requiring toxic heavy metals as catalysts (see, for example, J. March, Advanced Organic Chemistry, $3^{rd}$ Ed., John Wiley 1985, pp 1058, 813; ISBN 04718547-7; C. F. deGraauw, J. A. Peters, H. van Bekkum, J. Huskens, Synthesis, 1994, 1007-17; and S. D. Burke, D. L. Danheiser, Handbook of Reagents for Organic Synthesis, Oxidizing And Reducing Reagents, Wiley 1994; ISBN 0471979260.

A disadvantage is that the strongly basic reaction conditions lead to undesired aldol-type side reactions (see K. G. Akamanchi, B. A. Chaudhari, Tetrahedron Lett. 38, 6925-8 (1997)). Substrates sensitive to basic conditions cannot be reacted without decomposition (see T. Ooi, Y. Itagaki, T. Miura, K. Maruoka, Tetrahedron. Lett. 40, 2137-8 (1999)). Asymmetric variants of the MPV-Red that employ chiral transition metal catalysts for enantioselective hydrid transfer have been tested only on few model substrates and resulted in preparatively inacceptably low stereoselectivities (see F. Touchard, M. Bernard, F. Fache, F. Debbecq, V. Guiral, P. Sautet, M. Lemaire, J. Org. Met. Chem. 567, 133-6 (1998); und E. Breysse, C. Pinel, M. Lemaire, Tetrahedron: Asymmetry 9, 897-900 (1998)).

In contrast, biocatalytic methods have the advantage that they can be led under mild conditions, e.g. at room temperature and approximately neutral pH in aqueous media (see K. Faber, Biotransformations in Organic Chemistry $4^{th}$ Ed., Springer Verlag., Heidelberg 2000; ISBN 3-540-61688-8). An additional valuable property of biocatalysts is their normally high intrinsic stereoselectivity. In addition, the desired reaction usually takes place without side reactions. Biocatalytic redox processes on the basis of isolated alcohol dehydrogenases, however, require the presence of expensive cofactors, such as $NAD^+/NADH$ or $NADP^+/NADPH$. The recycling of these substrates is difficulty and expensive (see W. Hummel, Adv. Biochem. Eng./Biotechnol. 1997, 58, 145-184). One improvement of such processes is based on the presence of a second enzyme which, in the presence of a reducible or oxidizable component or cofactor, respectively, allows to recover the co-factor ("enzyme-coupled system", see W. Hummel, B. Riebel, Ann. N. Y. Acad. Sci. 1996, 799, 713-6). This variant, however, renders the process relatively complex and difficult to handle, as it is limited to such additives which are accepted as auxiliary component by the second enzyme. In addition, the concentrations of the substrates and the enzymes must be harmonized precisely for resulting in preparatively acceptable reaction rates. Furthermore, isolated enzymes usually have relatively short half lives under operating conditions. In order to achieve complete reaction into one direction, in the case of oxidation a carbonyl compound is added as reducible co-substrate in large molar excess, in the case of reduction a secondary alcohol as oxidizable co-substrate is added in large molar excess. This often results in difficulties especially with enzyme stability, as well as enzyme inhibition by the co-substrate.

If whole cells are used as biocatalysts in the stadium of fermentation, a lower addition of co-factors is required. In addition the cells are capable of recycling the co-factors themselves. However, the cells react very sensitively on high concentrations of organic substrates (substrate inhibition, solvent deactivation). For this reason, the biochemical MPV-Red and Op-Ox are limited to fermentative cells systems and low (co-)substrate concentrations (see G. Fantin, M. Fogagnolo, A. Medici, P. Pedrini, S. Fontana, Tetrahedron: Asymmetry 2000, 11, 2367-73). In general, the substrate concentrations are below 0.15 mol/l and the co-substrate concentrations below 3% (v/v) (see K. Nakamura, Y. Inoue, T. Matsuda, I. Misawa, J. Chem. Soc. Perkin Trans. I 1999, 2397-2402; and A. Goswami, R. L. Bezbaruah, J. Goswami, N. Borthakur, D. Dey, A. K. Hzarika, Tetrahedron: Asymmetry 2000, 11, 3701-9).

Reductions of ketones to the respective alcohols have also been conducted with acetone-pulverized *Geotrichum candidum* cells (see K. Nakamura, T. Matsuda, J. Org. Chem. 1998, 63, 8957-64). However, in this case, the cellular redox systens was partially inactivated during the freeze-drying of the cells. This required the addition of expensive redox-cofactors, such as $NAD^+/NADH$ or $NADP^+/NADPH$, for subsequent use as biocatalyst. The addition of (reducing) isopropyl alcohol as co-substrate was limited to about 3% (v/v) in that case. Due to the relatively low concentration of this organic co-solvent, the concentration of lipophilic ketone substrates could only be adjusted to a maximum of 0.4 mol/l.

In view of all these unsatisfying results which constitute an unmet need, there remains the problem to find novel, more efficient catalytic systems offering more ease of use, which diminish or remove the mentioned and other unfavorable disadvantages and allow to conduct redox reactions of alcohols to oxo (especially keto) compounds or the inverse reaction in an especially advantageous way.

It is thus an object of the present invention to provide novel catalytic systems that allow for avoiding the mentioned disadvantages and that have advantageous properties that allow for improved biocatalytic reduction of ketones and/or oxidation of secondary alcohols, respectively.

GENERAL DESCRIPTION OF THE INVENTION

The invention relates to a biocatalyst, especially an enzyme, preferably in (at least partially) purified form, which biocatalyst has alcohol dehydrogenase activity and which can be obtained from *Rhodococcus ruber*.

It has been found that this enzyme has unexpected and unique properties in comparison to other, known enzymes having the same type of activity. Especially, the novel enzyme has high temperature stability and in addition is capable of maintaining its activity in the presence of high concentrations of organic solvents (such as aromatic or aliphatic hydrocarbons, e.g. toluene, hexane) other than the co-substrates in up to 95, preferably up to 98% concentration (v/v). This especially allows for leading the oxidation or reduction reactions under conditions of high temperature and especially in the presence of high co-substrate concentrations (in the case of oxidation of alcohols, the presence of high ketone concentrations; in the case of reduction of ketones, the presence of high alcohol concentrations). It therefore allows for production on an industrially useful scale, especially avoiding many of the disadvantages mentioned for the reactions formerly described. Among the further advantages, a prolonged storage stability can be mentioned, as well as a high operational stability of catalytic activity. The enzyme is also capable of working also in the presence of complex-forming agents that usually would cause removal of bound catalytic metals like $Zn^{2+}$.

DETAILED DESCRIPTION OF THE INVENTION

Figure 1:
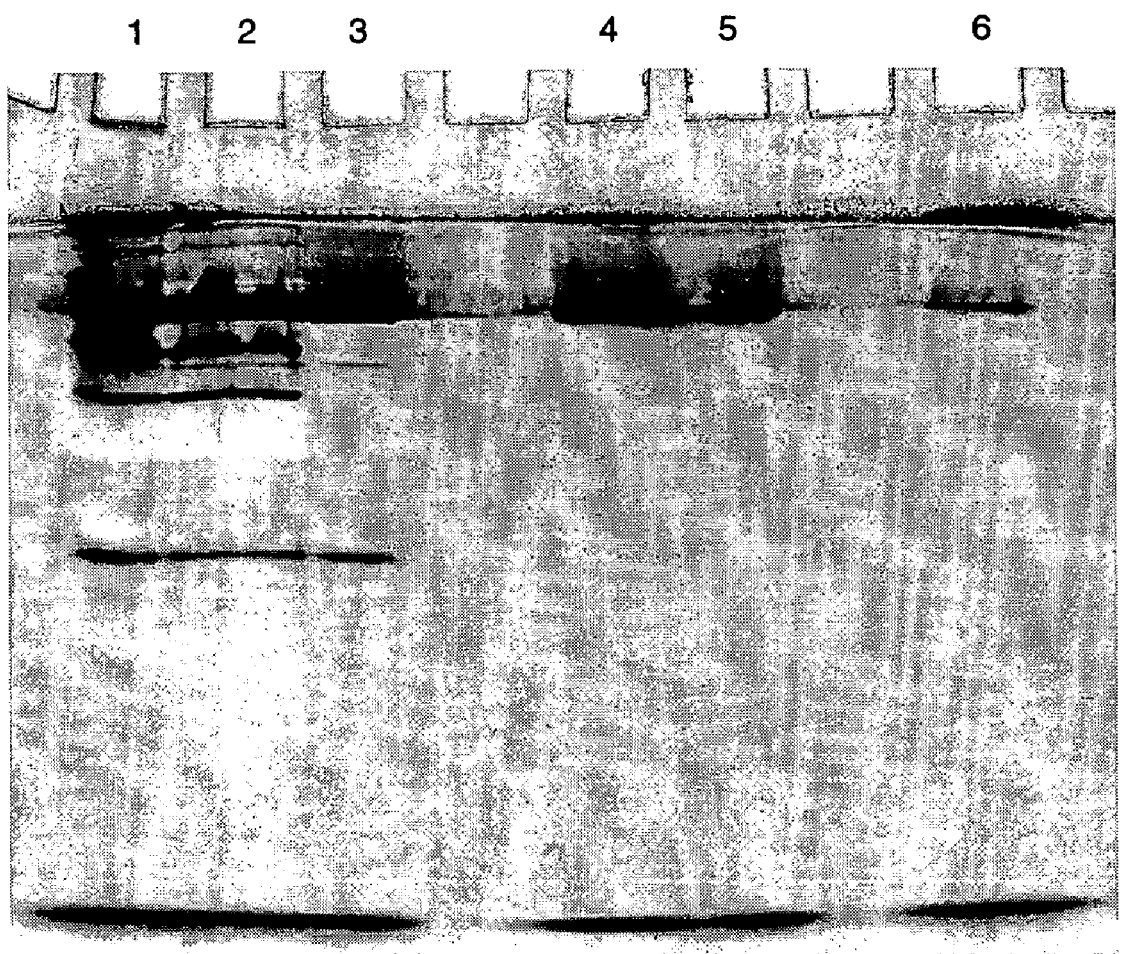
FIG. 1: Native gel analysis at different steps of the purification protocol of sec-alcohol dehydrogenase A. Lanes: Lane 1—crude cell extract; lane 2: batch DEAE cellulose; lane 3: Phenyl Sepharose; lane 4: UNO Q6; lane 5: Blue Sepharose; lane 6: Superdex 200.
Figure 2:
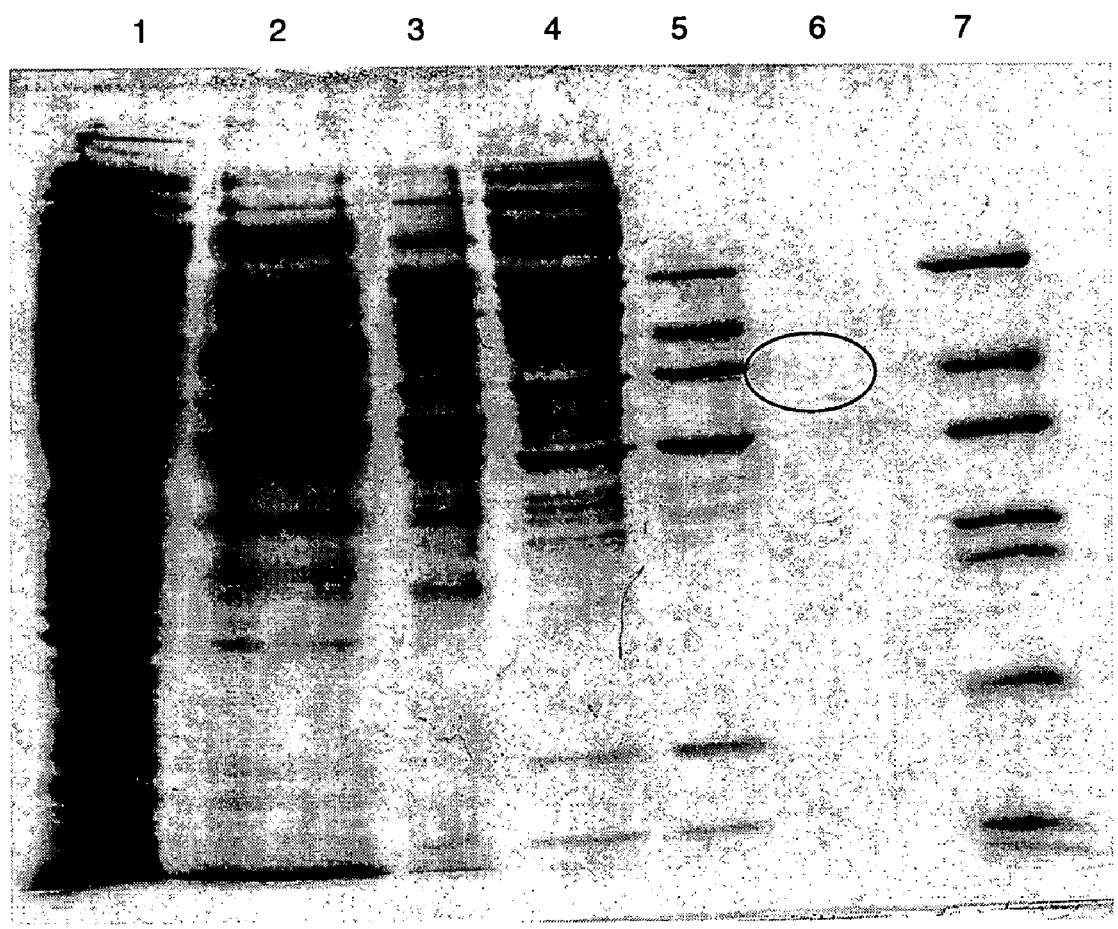
FIG. 2: SDS-PAGE analysis at different steps of the purification protocol of sec-alcohol dehydrogenase A. Lanes: Lane 1—crude cell extract; lane 2: batch DEAE cellulose; lane 3: Phenyl Sepharose; lane 4: UNO Q6; lane 5: Blue Sepharose; lane 6: Superdex 200; lane 7: low molecular weight standard.

The following are preferred embodiments of the invention:

The invention especially relates to an biocatalyst with alcohol dehydrogenase activity, especially an enzyme, preferably in (at least partially) purified form, which has alcohol dehydrogenase activity, especially stereospecific alcohol dehydrogenase activity in the oxidation of secondary alcohols or the reduction of ketones; and which can be obtained from a naturally occuring microorganism, especially *Rhodococcus*, especially *Rhodococcus ruber* DSM 44541 —called *Rhodococcus ruber* DSM 14855 hereafter, in accordance with the number of the Budapest Treaty deposit (see below).

The biocatalyst (or "enzyme") according to the invention is preferably present or used in purified form.

The invention also relates to a corresponding biocatalyst with alcohol dehydrogenase activity, obtained by recombinant technology (recombinant biocatalyst).

A further embodiment of the invention relates to the use of a biocatalyst with alcohol dehydrogenase activity according to the invention in the oxidation of secondary alcohols and/or the reduction of ketones (process of or according to the invention, hereinafter).

The process of the invention can be used especially for separating mixtures of stereo-isomers with respect to a center of chirality by kinetic resolution, if one stereo-isomer of an alcohol is specifically oxidized, or for the stereo-specific production of secondary alcohols having a specific chiral form from ketones.

Still a further embodiment relates to nucleic acids coding for such a biocatalyst with alcohol dehydrogenase activity, especially recombinant nucleic acids.

Another embodiment relates to microorganisms transformed with a nucleic acid coding for such a biocatalyst with alcohol dehydrogenase activity.

Further, the invention relates to the use of the mentioned microorganisms, especially host cells, in the production of said biocatalyst with alcohol dehydrogenase activity, as well as their use in the catalysis of the oxidation of secondary alcohols or the reduction of ketones, especially as shown in reaction scheme (A) below.

A further aspect of the invention relates to a (preferably isolated) polynucleotide, namely a DNA, or a (preferably isolated) recombinant polynucleotide comprising a DNA, each coding for a biocatalyst according to the invention, namely an enzyme, showing alcohol dehydrogenase activity, preferably as described above and below and in the examples as preferred, according to the invention which is characterized by the following sequence (SEQ ID NO: 47)

```
ATGAAAGCCG TCCAGTACAC CGAGATCGGC TCCGAGCCGG TCGTTGTCGA CATCCCCACC    60

CCGACGCCCG GGCCGGGTGA GATCCTGCTG AAGGTCACCG CGGCCGGGCT GTGCCACTCG   120

GACATCTTCG TGATGGACAT GCCGGCGGCG CAGTACGCCT ACGGCCTGCC GCTCACCCTC   180

GGCCACGAGG GTGTCGGCAC CGTCGCCGAA CTCGGCGAGG GCGTCACGGG ATTCGGGGTG   240

GGGGACGCCG TCGCCGTGTA CGGGCCGTGG GGCTGCGGTG CGTGCCACGC CTGCGCGCGC   300

GGCCGGGAGA ACTACTGCAC CCGCGCCGCC GACCTGGGCA TCACGCCACC CGGTCTCGGC   360

TCGCCCGGAT CGATGGCCGA GTACATGATC GTCGATTCGG CGCGCCACCT CGTCCCGATC   420

GGAGACCTCG ACCCGGTCGC CGCGGCGCCG CTCACCGACG CCGGTCTGAC GCCGTACCAC   480

GCGATCTCCC GGGTCCTGCC GCTGCTGGGG CCGGGCTCGA CGGCCGTCGT CATCGGTGTC   540

GGCGGGCTCG GCCACGTCGG CATCCAGATC CTGCGCGCCG TCAGCGCGGC CCGTGTGATC   600

GCCGTCGACC TCGACGACGA CCGTCTCGCC CTCGCCCGCG AGGTCGGCGC CGACGCGGCG   660

GTGAAGTCGG GCGCCGGTGC GGCGGACGCG ATCCGGGAAC TGACCGGCGG CCAGGGCGCG   720

ACGGCGGTGT TCGACTTCGT CGGCGCCCAG TCGACGATCG ACACGGCGCA GCAGGTGGTC   780

GCGGTCGACG GCACATCTC GGTCGTGGGC ATCCACGCCG GCGCACACGC CAAGGTCGGG   840

TTCTTCATGA TCCCGTTCGG CGCCTCCGTC GTGACCCCGT ACTGGGGCAC CCGGTCGGAA   900
```

```
CTGATGGAGG TCGTCGCGCT GGCCCGCGCC GGCCGGCTGG ACATCCACAC CGAGACGTTC    960

ACCCTCGACG AGGGGCCGGC GGCGTACCGG CGGCTGCGCG AGGGCAGCAT CCGCGGCCGC   1020

GGCGTGGTGG TTCCCTGA                                                 1038
```

(especially preferred) where in a broader embodiment of the invention also such versions of the polynucleotide or recombinant polynucleotide are comprised where conservative nucleic acid replacements that lead to no change in the resulting amino acid sequence are present as well as such changes in the base sequence that lead to amino acid replacements in the amino acid sequence resulting from translation thereof for 5% or less, preferably 3% or less of the total number of amino acids coded by and resulting from translation of the sequence of SEQ ID NO: 47, for example the replacement of up to 3 amino acids, provided that the resulting polypeptides still display an alcohol dehydrogenase activity as the biocatalyst according to the invention (especially the substrate specificities, ph-optimum, temperature optimum, temperature stability, activity in the presence of EDTA or solvent stability properties mentioned below, or any combination of two or more of these properties, preferably all these properties), especially with at least the high solvent and temperature stability mentioned below.

Preferably, exactly the DNA of SEQ ID NO: 47 is comprised, in a broader embodiment also variants thereof with up to 30, e.g. up to 15 nucleic acid replacements.

Any equivalents unobvious and novel over prior art (especially alcohol dehydrogenase) sequences (also, for example, those including modified nucleic acids but still having coding activity) are also comprised, even if this is not mentioned in the claims.

Also comprised are corresponding polynucleotides or recombinant polynucleotides comprising the mentioned otide, each as mentioned above coding for such a biocatalyst with alcohol dehydrogenase activity—preferably to microorganisms appropriate for expressing the gene, but also those that comprise the nucleic acid for pure conservation or replication purposes. The invention also relates to the use of and a method of using these micro-organisms (either living or killed, in complete or in at least partially digested form) especially in the oxidation or reduction reactions described above and below.

The invention also relates to the complementary nucleic acid for such a nucleic acid sequence as well as to double strands with both the complementary and the coding sequence.

A corresponding RNA (with U instead of T) is also comprised.

The invention also relates to the primers given in the examples under the SEQ ID Nos starting from SEQ ID NO 7 up to SEQ ID NO 46 and to the *Rhodococcus rubber* DSM 14855 DNA library mentioned in the examples.

Further, the invention also relates to a polypeptide showing alhohol dehydrogenase activity according to the invention (especially the substrate specificities, ph-optimum, temperature optimum, temperature stability and solvent stability properties mentioned below, or any combination of two or more of these properties, preferably all these properties), especially with at least the high solvent and temperature stability mentioned below, of the sequence with SEQ ID NO: 48

```
MKAVQYTEIG SEPVVVDIPT PTPGPGEILL KVTAAGLCHS DIFVMDMPAA QYAYGLPLTL    60

GHEGVGTVAE LGEGVTGFGV GDAVAVYGPW GCGACHACAR GRENYCTRAA DLGITPPGLG   120

SPGSMAEYMI VDSARHLVPI GDLDPVAAAP LTDAGLTPYH AISRVLPLLG PGSTAVVIGV   180

GGLGHVGIQI LRAVSAARVI AVDLDDDRLA LAREVGADAA VKSGAGAADA IRELTGGQGA   240

TAVFDFVGAQ STIDTAQQVV AVDGHISVVG IHAGAHAKVG FFMIPFGASV VTPYWGTRSE   300

LMEVVALARA GRLDIHTETF TLDEGPAAYR RLREGSIRGR GVVVP                   345
```

DNA sequence with insertions and/or deletions (either in addition to or alternatively to nucleic acid replacements), e.g. with a total of up to 300, preferably up to 90, for example up to 30 nucleic acids, preferably the insertions and deletions not affecting the reading frame, that is, resulting from addition or removal of one or more triplets, preferably in accordance with the mentioned boundaries, in each case provided that the resulting polypeptides after translation still display an alcohol dehydrogenase activity as the biocatalyst according to the invention.

In the case where a recombinant DNA comprising a DNA sequence coding for an enzyme showing alhohol dehydrogenase is mentioned, this is intended to include all vectors, such as plasmids, cosmids and the like, see also elsewhere in this specification.

The invention also relates to microorganisms transformed with a polynucleotide, especially a recombinant polynucle- as well as truncated or elongated versions thereof or those with amino acid replacements, especially of up to 5%, preferably up to 3% of the number of amino acids forming part of the sequence given under SEQ ID NO: 48, e.g. up to three amino acid replacements, especially but not necessarily of a conservative nature, and/or insertions, sequence extensions or deletions or combinations of two or more thereof, in each case preferably not exceeding a total of 100, preferably 30, for example up to 10 additional or deleted amino acids, provided that the resulting polypeptides still display an alcohol dehydrogenase activity as the biocatalyst according to the invention.

Any equivalents unobvious and novel over prior art (especially alcohol dehydrogenase) polypeptide sequences (also, for example, those including modified amino acids but still having alcohol dehydrogenase activity as defined for a biocatalyst according to the invention) are also comprised, even if this is not mentioned in the claims.

The invention also relates to the use of or a method of using such a polypeptide (in purified or at least partially purified form especially in the oxidation or reduction reactions described above and below.

The determination of the complete sequence for the polynucleotide requires an unusual combination of a very specific DNA extraction and the primer strategy described in the examples. Simple standard procedures are not successful.

Unless indicated otherwise, the general terms, symbols and names used in the description of the present invention preferably have the following meanings (where more specific definitions, in each case separately, or in combination, may be used to replace more general terms in order to define more preferred embodiments of the invention):

The invention especially relates to a biocatalyst with alcohol dehydrogenase activity, especially an enzyme, preferably in purified form, which has alcohol dehydrogenase activity and which can be obtained from *Rhodococcus ruber*, especially *Rhodococcus ruber* DSM 14855. That the biocatalyst has alcohol dehydrogenase activity, is not intended to mean that other activities (be it of enzymatic, regulatory or any other kind) are excluded within the present disclosure.

The terms "biocatalyst of the invention" or "enzyme of the invention" or "enzyme (or polypeptide) showing alhohol dehydrogenase activity", where used herein, relate to a biocatalyst having alcohol dehydrogenase activity, especially an enzyme with said activity, most especially alcohol dehydrogenase "ADH-A", as described below. If not stated otherwise, all these terms include not only the naturally occurring, "authentic" sequence of a polypeptide of the invention, which are the preferred embodiments of the invention, but also all mutants, variants and fragments thereof which exhibit the alcohol dehydrogenase activity, preferably with the same stereoselective activity as the natural enzyme.

An enzyme of the invention preferably has one, more preferably two, most preferably three or more of the following properties:

(i) Molecular weight on denaturing SDS polyacrylamide gel after electrophoresis: 30 to 45 kDa, especially about 38 kDa.

(ii) Molecular weight according to size exclusion chromatography (especially under the conditions mentioned in the examples) on Superdex 200: 55 to 69 kDa, especially about 62 kDa.

(iii) pH optimum in the reduction of ketones, especially of acetophenone in the presence of NADH: pH 6 to pH 7.

(iv) pH optimum in the oxidation of alcohols, especially of 1-phenylethanol in the presence of $NAD^+$: pH 8.5 to pH 9.5.

(v) Temperature optimum in the reduction of ketones, especially acetophenone in the presence of NADH: between 43 and 65° C.

(vi) Temperature optimum in the oxidation of secondary alcohols, especially 1-phenylethanol in the presence of $NAD^+$: between 43 and 65° C.

(vii) Temperature stability under the conditions just given for the temperature optimum, specifically with the substrates and co-substrates mentioned after "especially": at 50° C. less than 35% activity loss during 24 hours.

(viii) No activity change in the presence of EDTA (especially up to 5 mM concentration of EDTA) in an activity test at pH 7.5, 20 min incubation.

(ix) Presence of $Zn^{2+}$ bound to the molecule.

(x) Stability, especially alcohol dehydrogenase activity also in the presence of up to 50, preferably up to 80 percent by volume of isopropanol.

(xi) Stability, especially alcohol dehydrogenase activity also in the presence of up to 20, preferably up to 50 percent by volume of acetone.

(xii) Presence of the partial sequence EVGADAAAR (SEQ ID No: 1) within the total sequence of at least one polypeptide forming the whole or part of the enzyme.

(xiii) Presence of the partial sequence TD[L/I]FEVVA[L/I]AR (SEQ ID NO: 2) within the total sequence of at least one polypeptide forming the whole or part of the enzyme, where [L/I] is leucine or isoleucine.

(xiv) Presence of the partial sequence SGAGAADA[L/I]R (SEQ ID NO: 3) within the total sequence of at least one polypeptide forming the whole or part of the enzyme, where [L/I] is leucine or isoleucine.

(xv) Presence of the partial sequence V[L/I]AVD[L/I]DDDE (SEQ ID NO: 4) within the total sequence of at least one polypeptide forming the whole or part of the enzyme, where [L/I] is leucine or isoleucine.

(xvi) Presence of the partial sequence V[L/I]AVD[L/I]DDDXRX (SEQ ID NO: 5) within the total sequence of at least one polypeptide forming the whole or part of the enzyme, where [L/I] is leucine or isoleucine and X stands for an unidentified amino acid.

(xvii) Presence of the partial sequence [TD/DT] [L/I]MEVVA[L/I]AR (SEQ ID NO: 6 (either with TD in the beginning=at the amino terminus or with DT in the beginning) within the total sequence of at least one polypeptide forming the whole or part of the enzyme where the sequence in brackets is selected from the two alternatives mentioned therein and [L/I] is isoleucine or leucine.

Especially preferred among these properties are those mentioned under (x) and/or (xi).

The term "within the total sequence of at least one polypeptide forming the whole or part of the enzyme" refers to the possibility that the biocatalyst/enzyme according to the invention may consist of one subunit (then it is formed from one polypeptide) or more than one (identical or different) subunits (then it is formed from the corresponding number of polypeptides).

More preferred is an enzyme of the invention wherein one of the partial sequences mentioned under (xii) to (xvii) is present or wherein one of the amino acids mentioned in any of these sequences is exchanged against a different amino acid, preferably by a conservative replacement, e.g. of lipophilic against lipophilic, basic against basic, acidic against acidic, polar against polar amino acids, or the like.

Still more preferred is an enzyme the peptide sequence or, if more than one different subunits are present, sequences of which comprise a partial sequence selected from two, more preferably 3, even more preferably 4, still most preferably 5, most preferably 6 of the sequences mentioned above under (xii) to (xvii).

The enzyme of the invention is isolated (purified) from the microorganism by methods that are, per se, well known in the art, in particular by the methods described in the examples or methods analogous thereto, the whole purification method also forming an embodiment of the invention.

The Alcohol dehydrogenase activity is preferably determined by oxidation of 1-phenylethanol (6.6 μM) and addition of 10 mM $NAD^+$ (testing conditions: 30° C., 10 μM Trisbuffer, pH 7.5, 10 min, conversion by GC-analysis), or as described in the Examples.

A biocatalyst of the invention is obtainable from a naturally occurring microorganism fermentable by a process comprising inoculating a selection medium with natural samples such as soil, water, or plant silage, preferably a hydrocarbon, e.g. hexane. Apart from the carbon source, the selection medium also contains all essential ingredients necessary for allowing growth of microorganisms, such as mineral salts, N-sources, and trace elements.

A naturally occurring microorganism having alcohol dehydrogenase activity can be obtained by a process known in the art, for example by isolation from a natural source, such as Rhine water.

In order to obtain the purified enzyme of the invention, the microorganism having alcohol dehydrogenase activity, especially *Rhodococcus ruber* DSM 14855, is cultivated in an aqueous nutrient medium, e.g. comprising yeast extract, peptone, glucose and mineral salts (e.g. 10 g/l yeast extract 10 g/l peptone, 2 g/l NaCl, 0.15 g/l MgSO$_4$.7H$_2$O, 1.3 g/l NaH$_2$PO$_4$, 4.4 g/l K$_2$HPO$_4$) for some, e.g. three, days. Cell growth is followed by determination of the optical density via absorption, e.g. at 546 nm.

The cells are disrupted, the biomass is removed and the cell-free extract is obtained. The fermentation time is so selected that optimum titers with respect to alcohol dehydrogenase activity are achieved.

When the cell density has reached an adequate value, the cultivation is discontinued. The culture broth is separated off in known manner, e.g. by centrifugation, and the sedimented cells are broken down in customary manner, e.g. by shaking with fine glass beads, by ultra-sound treatment, or using a French press. Insoluble cell components and, if used, glass beads, are removed, e.g., by centrifugation, and the residue is used as the enzyme source (crude extract). The residue, as an alcohol dehydrogenase activity-containing crude extract, can be used directly in the process according to the invention. Advantageously, however, in order to remove nucleic acids (viscous solutions) and other impurities or interfering components (e.g. other dehydrogenases with lower steric selectivity) the crude extract is subjected to further purification in order to obtain the enzyme of the invention in purified form. Preferably, the crude cell extract is subjected to one or more purification steps that, as such, are known in the art in order to remove interfering components from the extract.

A preferred method makes use of batch pretreatment with a cation exchanger, e.g. DEAE cellulose, and subsequent chromatographic (especially FPLC) separation first by Hydro-phobic Interaction Chromatography, e.g. over Phenyl Sepharose, advantageously after removing precipitations formed in the presence of (NH$_4$)$_2$SO$_4$. With increasing (NH$_4$)$_2$SO$_4$ content of the eluent, enzyme activity is eluted. The active fractions are further separated by anion exchange chromatography, preferably on an UNO Q column (BioRad). Elution by eluents with increasing sodium chloride content yields again active fractions with alcohol dehydrogenase activity. The interesting fractions are then further purified on a separation matrix comprising binding places for adenylyl-comprising cofactors, e.g. carrying the dye Cibacron Blue F3G-A or other moieties allowing for such affinity chromatography, especially using Blue Sepharose CI-6B, this innovative material allowing a surprisingly good further purification, although surprisingly no binding takes place. This adds to the information showing surprising properties of the enzyme according to the invention. The next step is size exclusion chromatography, e.g. using a Superdex 200 column. Here the enzyme of the invention elutes in fractions corresponding to a molecular weight between 55 to 69 kDa, with an average of about 62 kDa.

The term "purified" means preferably "in at least partially purified form" or "in enriched form" or, more preferably, purified in the stricter sense, that is, in practically isolated form (especially with more than 50, most especially more than 95% purity by weight compared to other peptides present).

A corresponding biocatalyst with alcohol dehydrogenase activity, obtained by recombinant technology, then called a recombinant biocatalyst of the invention, (or also a biocatalyst from natural sources other than *Rhodococcus ruber* DSM 14855), preferably is defined as follows. The sequence of said biocatalyst may comprise deletions, insertions, terminal additions or exchanges (especially conservative exchanges, e.g. of lipophilic against lipophilic, basic against basic, acidic against acidic, polar against polar amino acids, or the like) of amino acids (preferably of up to 20, in case of terminal additions up to 1000; more preferably of up to 5, in case of terminal additions of up to 200 amino acids, respectively), or any combination of such changes, when compared to the sequence of the enzyme as purified in the examples or possible different subunits thereof, as long as the basic activity (alcohol dehydrogenase activity, especially with the substrates (preferably 1-phenylethanol or acetophenone) and co-substrates mentioned in the examples) is still present, especially in connection with one or more of the additional advantageous properties mentioned for a biocatalyst according to the invention. Also, modified amino acids (with different structures than the 20 amino acids directly derivable from the genetic code) which may be modified during translation or post-translationally, may be present, e.g. 1 to 20, more preferably 1 to 5 such amino acids.

In a preferred embodiment of the use a biocatalyst with alcohol dehydrogenase activity in the oxidation of secondary alcohols or the reduction of ketones is the use in catalyzing the following reactions (reaction scheme (A)):

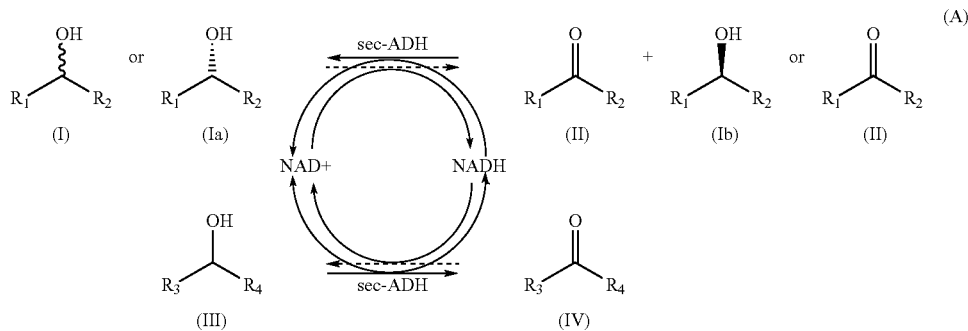

wherein, in formula I, Ia and Ib, $R_1$ and $R_2$ are two different moieties from the group consisting of unsubstituted or substituted alkyl, unsubstituted or substituted alkenyl, unsubstituted or substituted alkinyl, unsubstituted or substituted cycloalkyl, unsubstituted or substituted aryl and unsubstituted or substituted heterocyclyl, or $R_1$ and $R_2$ together form an unsubstituted or substituted bridge; and in formula III and formula IV, $R_3$ and $R_4$ are two different or preferably two identical lower alkyl or aryl moieties, or together form a bridge.

The term "lower" defines a moiety with up to and including maximally 7, especially up to and including maximally 4, carbon atoms, said moiety being branched or straight-chained. Lower alkyl, for example, is ethyl, n-propyl, sec-propyl, n-butyl, isobutyl, sec-butyl, tert-butyl, n-pentyl, n-hexyl or n-heptyl or most preferably methyl.

"Substituted", wherever used for a moiety, means that one or more hydrogen atoms in the respective molecule, especially up to 5, more especially up to three, of the hydrogen atoms are replaced by the corresponding number of substituents which preferably are independently selected from the group consisting of alkyl, especially lower alkyl, for example methyl, ethyl or propyl, fluoro-lower alkyl, for example trifluoromethyl, $C_6$-$C_{16}$-aryl, especially phenyl or naphthyl (where $C_6$-$C_{16}$-aryl, especially phenyl or naphthyl, is unsubstituted or substituted by one or more, especially up to three moieties selected from halogen, carboxy, lower alkoxycarbonyl, hydroxy, lower alkoxy, phenyl-lower alkoxy, lower alkanoyloxy, lower alkanoyl, amino, N-lower alkylamino, N,N-di-lower alkylamino, N-phenyl-lower alkylamino, N,N-bis-(phenyl-lower alkyl)-amino, lower alkanoylamino, fluoro-lower alkyl, e.g. trifluoromethyl, and sulfo), $C_3$-$C_{10}$-cycloalkyl (that is unsubstituted or substituted by one or more, especially up to three moieties selected from halogen, carboxy, lower alkoxycarbonyl, hydroxy, lower alkoxy, phenyl-lower alkoxy, lower alkanoyloxy, lower alkanoyl, amino, N-lower alkylamino, N,N-di-lower alkylamino, N-phenyl-lower alkylamino, N,N-bis(phenyl-lower alkyl)-amino, lower alkanoylamino, fluoro-lower alkyl, e.g. trifluoromethyl, and sulfo), heterocyclyl that is unsaturated, saturated or partially saturated, is mono-, bi- or tri-cyclic and has 4 to 16 ring atoms, where instead of one or more, especially one to four, carbon ring atoms the corresponding number of heteroatoms are present (within the chemically possible limits) selected from nitrogen, oxygen and sulfur (with said heterocyclyl unsubstituted or substituted by one or more, especially up to three moieties selected from halogen, carboxy, lower alkoxycarbonyl, hydroxy, lower alkoxy, phenyl-lower alkoxy, lower alkanoyloxy, lower alkanoyl, amino, N-lower alkylamino, N,N-di-lower alkylamino, N-phenyl-lower alkylamino, N,N-bis(phenyl-lower alkyl)-amino, lower alkanoylamino, fluoro-lower alkyl, e.g. trifluoromethyl, and sulfo), hydroxy, lower alkoxy, for example methoxy, phenyl-lower alkoxy, lower alkanoyloxy, amino, N-lower alkylamino, N,N-di-lower alkylamino, N-phenyl-lower alkylamino, N,N-bis-(phenyl-lower alkyl)-amino, lower alkanoylamino, carbamoyl-lower alkoxy, N-lower alkylcarbamoyl-lower alkoxy or N,N-di-lower alkylcarbamoyl-lower alkoxy, amino, mono- or di-lower alkylamino, lower alkanoylamino, carboxy, lower alkoxycarbonyl, phenyl-, naphthyl- or fluorenyl-lower alkoxycarbonyl, such as benzyloxycarbonyl, lower alkanoyl, sulfo, lower alkanesulfonyl, for example methanesulfonyl ($CH_3$—$S(O)_2$—), phosphono (—$P(=O)(OH)_2$), hydroxy-lower alkoxy phosphoryl or di-lower alkoxyphosphoryl, carbamoyl, mono- or di-lower alkylcarbamoyl, sulfamoyl and mono- or di-lower alkylaminosulfonyl. It goes without saying that substitutents are only at positions where they are chemically possible, the person skilled in the art being able to decide (either experimentally or theoretically) without inappropriate effort which substitutions are possible and which are not. Where more than one substituent is present, the substituents, if not indicated otherwise, are selected independently from each other.

Alkyl preferably has up to 24, more preferably up to 12 carbon atoms and, if possible in view of the number of carbon atoms, is linear or branched one or more times; preferred is lower alkyl, especially $C_1$-$C_4$-alkyl. Alkyl can be substituted or unsubstituted, especially by one or more, more especially up to 3, of the substituents mentioned above under "substituted". Unsubstituted alkyl, especially lower alkyl, is one preferred embodiment.

Alkenyl is preferably a moiety with one or more double bonds and preferably has 2 to 20, more preferably up to 12, carbon atoms; it is linear or branched one or more times (as far as possible in view of the number of carbon atoms). Preferred is $C_2$-$C_7$-alkenyl, especially $C_3$-$C_4$-alkenyl, such as allyl or crotyl. Alkenyl can be unsubstituted or substituted, especially by one or more, more especially up to three, of the substituents mentioned above under "substituted". Substituents such as amino or hydroxy (with free dissociable hydrogen) preferably are not bound to carbon atoms that participate at a double bond, and also other subtituents that are not sufficiently stable are preferably excluded. Unsubstituted alkenyl, in particular $C_2$-$C_7$-alkenyl, is especially preferred.

Alkinyl is preferably a moiety with one or more triple bonds and preferably has 2 to 20, more preferably up to 12, carbon atoms; it is linear of branched one or more times (as far as possible in view of the number of carbon atoms). Preferred is $C_2$-$C_7$-alkinyl, especially $C_3$-$C_4$-alkinyl, such as ethinyl or propin-2-yl. Alkinyl can be unsubstituted or substituted, especially by one or more, more especially up to three, of the substituents mentioned above under "substituted". Substituents such as amino or hydroxy (with free dissociable hydrogen) preferably are not bound to carbon atoms that participate at a triple bond, and also other subtituents that are not sufficiently stable are preferably excluded. Unsubstituted alkinyl, in particular $C_2$-$C_7$-alkinyl, is especially preferred.

Aryl preferably has a ring system with not more than 20 carbon atoms, especially not more than 14 carbon atoms; is preferably mono-, bi- or tricyclic; and is unsubstituted or substituted by one or more, especially up to three, substitutents, preferably as defined above under "substituted". For example, aryl is selected from the group consisting of phenyl, naphthyl, indenyl, azulenyl and anthryl, each of which is unsubstituted or substituted; preferably from phenyl or 1- or 2-naphthyl, each unsubstituted or substituted by one or more, preferably up to 5, substituents as defined above under "substituted".

Heterocyclyl is preferably a heterocyclic radical that is unsaturated, saturated or partially saturated, and is preferably a monocyclic or, in a broader aspect of the invention, bi- or tri-cyclic moiety; it has preferably 3 to 24, especially 4 to 16 carbon atoms, where instead of one or more, especially one to four, carbon ring atoms the corresponding number of heteroatoms are present, especially (within the chemically possible limits) selected from nitrogen, oxygen and sulfur; and where heterocyclyl is unsubstituted or substituted by one or more, especially up to three, substituents as defined above under "substituents". Preferably heterocyclyl is selected from the group consisting of oxiranyl, azirinyl, 1,2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, pyranyol, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, indolizinyl, isoindolyl, 3H-indolyl, indolyl, benzimidazolyl, cumaryl, indazolyl, triazolyl, tetrazolyl, purinyl, 4H-chinolizinyl, isochinolyl, chinolyl, tetrahydrochinolyl, tetrahydroisochinolyl, decahydrochinolyl, octahydroisochinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, β-carbolinyl, phenanthridinyl, acridinyl, perimidinyl, phenanthrolinyl, furazanyl, phenazinyl, phenothiazinyl, phenoxazinyl, chromenyl, isochromanyl and chromanyl, where each of these moieties is unsubstituted or substituted as described above, especially by one or more moieties selected from lower alkyl, especially methyl, lower alkoxy, especially methoxy, halogen, especially fluoro, chloro, bromo or iodo, and halogen-lower alkyl, especially trifluoromethyl.

Cycloalkyl preferably has 3 to 12, more preferably 3 to 8 carbon atoms and is, for example, cyclopropyl, cyclobutyl, cyclopentyl, cyclohexyl or cycloheptyl; it is unsubstituted or substituted with one or more, especially up to 3, substituents, preferably as defined above under "substituted".

An unsubstituted or substituted bridge formed from $R_1$ and $R_2$ in formula I, Ia, Ib or II is preferably a bridge formed by 2 to 12 carbon atoms that, together with the binding atom in formula I, Ia, Ib or II forms a ring; where the bridge may contain one or more double and/or triple bonds at places other than the binding carbon atom (then the bridge has at least three carbon atoms) or is preferably saturated. The substituents are preferably chosen from 1 or more, especially up to three, substituents as defined under "substituents". Most preferred is a $C_2$-$C_7$-alkylen chain, such as ethylene, propylene, n-butylene, n-hexylene or n-heptylene, each of which is substituted by one or more, especially 1 or 2, of the moieties defined above under "substituted", or preferably is unsubstituted.

As far as compounds (including alcohols, ketones, substrates, co-substrates and the like) are mentioned herein, this includes also the corresponding salts or solvate salts thereof, if salt-forming compounds are present, as well as the corresponding solvates. Salt forming groups are especially basic groups, such as amino groups, or acidic groups, such as carboxy groups. In the case of acidic groups, the corresponding metal salts, such as alkaline metal salts, e.g. sodium or potassium salts, or alkaline-earth metal salts, such as calcium salts, or salts with nitrogen bases, such as ammonium-, trilower alkylammonium, pyridinium salts or the like, can be present; in the case of basic groups, the corresponding acid addition salts may be present, e.g. with inorganic acids, such as sulphuric acid or hydrogen halides, such as HCl or HBr, or with organic acids, e.g. carboxylic acids, such as acetic acid, or sulfonic acids, e.g. methane sulfonic acid.

Examples for preferred secondary alcohols are hydroxy group carrying isoprenoids, such as mono-, di- or tri-terpenes, e.g. geraniol, isoborneol, ipsenol, menthol (especially (±)menthol), nerolidol, hernandulcin, taxol or lanosterol, or steroids, such as cholestan-3-ol, cholesterol, ergosterin, stigmasterin, cholic acids, vitamin $D_2$, vitamin $D_3$, androsterone, testosterone, estrone, 17β-estradiol, estriol, cortisol, corticosterone, aldosterone, triamincolone, digitoxigenin, strophanthidine, ouabagenine, scillaridine or bufotalin; di-lower alkyl- or lower alkyl-lower alkenyl methanols, such as iso-propanol, butane-2-ol, n-hexane-2-ol, n-heptane-2-ol, n-octane-2-ol, n-nonane-2-ol, 3-octanol, 5-methyl-2-heptanol, 3-octen-2-ol or 6-methyl-hex-5-en-2-ol; or n-decane-2-ol; R-, S- or R,S-1-phenyl-1-ethanol, benzhydrol, R-, S- or R,S-1-(1- or 2-naphthyl)-1-ethanol, R-, S- or R,S-1-phenyl-2-butanol, wherein the naphthyl or phenyl moieties are unsubstituted or substituted by one or more, preferably up to 5, substituents independently selected from lower alkoxy, such as methoxy, lower alkyl, such as methyl, nitro, cyano, halogen, such as fluorine, chlorine, bromine or iodine, or halo-lower alkyl, such as trifluoromethyl; cyclopentanol, R-, S- or R,S-1-hydroxyethylcyclohexane or the like.

Preferred cosubstrates for the reduction are secondary alcohols, such as isopropanol, 4-methyl-2-pentanol or further other C,C-di-(lower alkyl)-methanols. These are preferably present in the reaction mixture in an excess, for example compared to the ketone to be reduced, for example making up 50% (related to the volume of the reaction mixture, v/v). The concentration of the ketone to be reduced preferably lies below an upper limit of 3 mol/l, preferably up to 2.6 mol/l or lower.

Ketones to be reduced are especially free ketones or ketals thereof (such as especially di-(loweralkyl) ketals or (cyclic) (unsubstituted or substituted, for example by lower alkyl, such as methyl) lower alkylene ketals, such as ethylene ketals (dioxolan derivatives).

Examples are oxo-carrying isoprene derivatives, such as mono-, di- or triterpenes, e.g. menthone, pulegone, carvone, carone, verbenone, camphor, dihydrocarvone, dihydrocarvone hydrobromide, carvenone, hernandulcine or taxol or lanosterol, or steroids, such as androsterone, testosterone, estrone, cortisol, corticosterone, aldosterone or prednisone; di-(lower alkyl)- or lower alkyl-lower alkenyl-ketones, such as acetone, butan-2-one, n-hexan-2-one, n-heptan-2-one, n-octan-2-one, n-nonan-2-one, 3-octanone, 5-methyl-2-heptanone, 3-octen-2-one, 3-penten-2-one, 6-methyl-hex-5-en-2-one or 6-methyl-hept-5-en-2-one; hydroxyacetone; or n-decan-2-one; acetophenone, methyl-1-(1- or 2-naphthyl) ketone, methyl-1-phenylmethyl-ketone, 1-phenyl-2-propanone, benzophenone or phenacyl halogenides, wherein the naphthyl- or phenyl moieties in the moieties mentioned are in each case unsubstituted or substituted by one or more, preferably one to five substituents selected independendently of each from the group consisting of lower alkoxy, such as methoxy, lower alkyl, such as methyl, nitro, cyano, halogen, such as fluorine, chlorine, bromine or iodine, or halo-lower alkyl, such as trifluoromethyl; 2-furylethanone; cyclopentanone, cyclohexanone, 2-methylcyclohexanone, cycloheptanone, methyl-cyclohexylketone; keto esters, such as methylpyruvate, ethylpyruvate, ethyl-bromopyruvate, ethyl-3-methyl-2-oxobutyrate, ethyl-3-oxo-butyrate, methyl-3-oxobutyrate, phenylglyoxylic acid methylester, phenylglyoxalic acid ethylester, 2-oxo-4-phenylbutyric acid methylester or the corresponding tert-butyl- or neopentyl ester.

For the use according to the invention in the oxidation or reduction in the presence of the biocatalyst according to the invention, customary conditions for chemical reactions of that type are chosen.

The preferred pH range for the oxidation of alcohols in the presence of ketones as co-substrates is kept in the area from pH 6 to pH 12, more preferably from pH 8 to pH 11. For the reduction, the preferred pH range lies between pH 5 and pH 9, more preferably between pH 6 and pH 8. The pH value is controlled by standard buffers, for example phosphate buffers with alkaline metal, especially potassium or sodium phosphate buffer, boronic acid/HCl/sodium hydroxide buffers, or other buffers, such as Tris/HCl, HEPES buffers or the like;

and/or by automated titration with an acid, such as HCl, to keep the pH from rising, or a base, such as NaOH, to keep the pH from sinking.

The amount of the enzyme used is adapted to the amount of the substrate to be converted and can be calculated conveniently from the activity of the biocatalyst according to the invention (see e.g. purification table=Table 3 in Example 2).

The enzyme of the invention can also be used in the presence of surface active substances (surfactants, detergents). As detergents, for example,

- anionic tensides, that usually include long chain fatty acids as anionic, hydrophobic component, e.g. sulfates of long chain (especially $C_8$-$C_{18}$) alcohols, such as alkaline metal $C_8$-$C_{18}$alkanoylsulfates, especially sodium dodecylsulfate or sodium decylsulfate;
- cationic tensides, which besides hydrophobic, aliphatic or aromatic (especially alkyl) moieties include hydrophilic groups with a positive charge (e.g. quaternary ammonium), such as benzyl-dimethylstearylammonium chloride or cetylpyridinium chloride;
- amphoteric detergents, such as mono- or dicarboxylated imidazolines of fatty acids, such as sodium lauryidicarboxyimidazoline or sodium; or
- non-ionic tensides, such as ethoxylated sugar esters of higher fatty acids, such as polyoxyethylene-sorbitan-monolaurate, -palmitate, -stearate or -tristearate.

The temperatures for the use of the enzyme of the invention in the oxidation or reduction reactions preferably lies in the range customary for biocatalytic reactions or above, preferably in the range from 10 to 65, more preferably from 40 to 65°C.

A preferred embodiment of the use according to the invention is in the steroselective (enantioselective or, in the presence of more than one center or axis of asymmetry, diastereoselective) production of chiral (or diastereomeric) alcohols from the corresponding ketones (especially of the formula II wherein $R_1$ and $R_2$ have different meanings) or form an asymmetric (e.g. asymmetrically substituted) bridge with prochiral oxo-carrying carbon by reduction of the prochiral C=O group. The oxidation of or reduction to the S-enantiomer is especially preferred in this reaction. Enantiomeric purities in excess of 90%, especially of 96% (in terms of the enantiomeric excess=ee=100 (2x−1) where x is the molar fraction of the prevailing enantiomer) or more, most preferably of 99% or more, are obtained with the enzyme of the invention.

Yet another preferred embodiment of the invention relates to the use of/process using the enzyme of the invention for the (mild) chemoselective (especially stereoselective) oxidation of secondary alcohols, where only the hydroxy group with the appropriate steric form is oxidised to the corresponding oxo group (while other oxidable hydroxy groups in the same or other molecules remain intact). This can especially be used for the separation of isomers where from mixtures of alcohols only the reactive ones are oxidised, so that either the desired alcohols remain as such or the resulting oxo compounds are, in a subsequent step, again transformed into the desired alcohols by reversal of the reaction (reduction).

An especially preferred variant of this use (process) relates to the use of an enzyme according to the invention for the (mild) enantioselective oxidation of only one isomer of mixtures of enantiomers (or diastereomers), especially racemates, of secondary alcohols, especially of alcohols of the formula I wherein $R_1$ and $R_2$ are two different moieties, especially as defined above, or form an asymmetric (especially asymmetrically substituted) bridge. By this method, the remaining alcohol can be obtained in isomerically pure, especially enantiomerically pure, form, e.g. with 75% or more, especially 95% or more, more especially with 98% or more enantiomeric excess regarding the carbon atom carrying $R_1$ and $R_2$.

The process of the invention can thus be used especially for separating mixtures of stereoisomers with respect to a center of chirality by kinetic resolution, if one stereoisomer of an alcohol is specifically oxidized, or for the stereospecific production of secondary alcohols representing a specific chiral form from ketones.

Still another preferred embodiment of the invention relates to the use of/ a process using an enzyme of the invention for the mild chemoselective reduction of ketones where only specific oxo groups are converted into the corresponding secondary hydroxy group(s), while other reducible groups (less amenable keto groups, C=C double bonds, nitro groups or the like) remain intact. This can also be used for separation processes in that from complex mixtures of ketones only the reactive ones are taking part in the reaction while either the desired oxo compounds remain in the reaction mixtures or the resulting alcohols are, in a subsequent inverse step (oxidation), converted back into the desired keto compounds. As in that reaction prochiral oxo-substituted carbon atoms are transformed into the corresponding asymmetrically substituted hydroxy-carrying carbon atoms, this is also appropriate for obtaining the isomerically, especially enantiomerically, pure alcohols (especially with a purity as defined above).

The process of the invention can be performed with free or immobilized biocatalyst according to the invention, which can be used in enriched or preferably in purified form. In another embodiment of the invention a recombinant microorganism (especially a host cell) which is present in suspension or immobilized and is expressing an enzyme of the invention is used for performing the reaction, i.e. the enzyme is in cell-bound form.

For example, an enzyme of the invention for use in a process of the invention may be immobilized. The immobilization of said enzyme can be carried out analogously to processes known per se, e.g. coupling to a solid support or enclosing in an enzyme membrane reactor.

The process of the invention may also be lead in the presence of a (free or immobilized) microorganism transformed by genetic engineering techniques with a gene coding for an enzyme of the invention to be able to produce the desired enzyme of the invention, especially in higher amounts than it would be present in the original microorganism, e.g. *Rhodococcus ruber*, especially *Rhodococcus ruber* DSM 14855.

The reaction of an alcohol or ketone substrate with an enzyme of the invention or a microbial cell extract is preferably carried out in homogeneous aqueous solution at pH 5 to 10.5, more preferably at pH 6 to 9.5. For the stabilization of the pH value, the reaction is carried out in a manner known per se in buffered solution or using a pH-stat. The reaction temperature is approximately from 10 to 65° C., more preferably from 20 to 50° C., even more preferably from 20 to 30° C. The substrate is used preferably in a concentration of 1 mM to 2 M, more preferably 50 mM to 500 mM. However, if the substrate is less soluble, it is also possible to use a substrate suspension.

The process according to the invention can be carried out either as a batch process or continuously in an enzyme membrane reactor (EMR). In the latter case, the enzyme membrane reactor is preferably fitted with an ultrafiltration membrane having a separation limit of less than approximately 30 000 Da, so that the enzymes contained in the reaction mixture are held back whilst the low-molecular-weight products and unreacted reactants pass through the membrane and the product can be isolated from the outflow. The reactor is preferably sterilized before use so that the addition of antibacterial substances can be dispensed with. The reactions are carried out in a manner analogous to that described above.

The process according to the invention can also be carried out by percolating the solution containing the alcohol or ketone substrate, which has been adjusted to a suitable pH value, through a solid carrier on which the enzyme of the invention has been immobilized (the matrix-bound enzyme preparation is obtainable, for example, by percolation of the crude microbial extract through CNBr-activated Sepharose, Eupergit or the like).

Working up the reaction mixture and purification of the products in accordance with the invention are carried out by customary processes known from the State of the Art. For example, the reaction mixture can be clarified by filtration or, preferably, centrifugation, and then the enzyme can be separated by ultrafiltration (membrane with separation limit of $\leqq 30$ kDa) and the remaining product can be washed out of the retentate by diafiltration.

The isolation of the desired products obtained according to any of the variants of the use of or process using the enzyme of the invention (secondary alcohol or ketone) is achieved using standard methods, such as distillation or rectification (fractionated distillation), steam distillation or azeotropic distillation, or using chromatographic methods, just to recite some examples to which the skilled person may add other methods as convenient or necessary.

Salts of educts or products can be converted into the free compounds, free compounds into the salts using standard methods, respectively.

Nucleic acids are preferably DNA or RNA (in general, oligo- or polynucleotides).

Isolated nucleic acids coding for a biocatalyst according to the invention with alcohol dehydrogenase activity, especially recombinant nucleic acids, are preferably obtained and defined as follows:

A nucleic acid, especially a gene, coding for a biocatalyst of the invention can, for example, be obtained by identifying at least a part of the sequence of an isolated enzyme of the invention, deducing DNA sequences coding for the partial protein sequence, preparing an oligonucleotide or a mixture of oligonucleotides (taking into consideration the degeneracy of the genetic code) as probe(s), probing a DNA library derived from the microbial strain naturally expressing the activity of the biocatalyst (the term DNA library also including a "cDNA-library"), isolating the gene, and cloning it into a suitable vector for transformation of the microorganism to be genetically modified. All these methods (especially those depicted below for identification of, transformation with and expression of nucleic acids coding for an enzyme of the invention) are standard practice, e.g. as described in Sambrook et al., Molecular Cloning—A Laboratory Manual, $2^{nd}$ edition, Cold Spring Harbor Press, 1989, or in in Gassen et al., "Gentechnische Methoden—Eine Sammlung von Arbeitsanleitungen für das molekularbiologische Labor", Spektrum Akademischer Verlag, Heidelberg 1999, in F. M. Asubel (Hg.) "Short Protocols in Molecular Biology", $3^{rd}$ ed., New York, Wiley 1997; or in Asubel et al., "Current Protocols in Molecular Biology", Vol. 1-3, Greene Publishing Associates and Wiley-Interscience, New York, 1987.

The partial sequencing of an enzyme of the invention is, for example, made using selective endoproteases for selective digestion, e.g. endo-protease Lys-C, endoprotease Glu-C, chymotrypsin, thermolysin or preferably trypsin (cleaving C-terminally from the basic amino acids arginine or lysine) and, after separation, e.g. electrophoretically on a gel or by chromatography (e.g. HPLC), determining the terminal sequences of the resulting peptides, e.g. by exopeptidases, e.g. carboxypeptidases, such as carboxypeptidase A, B or P). Preferred is tryptic digestion, then MS/MS analysis (TOF).

DNA libraries can also be obtained by PCR methods.

A cDNA library (obtainable e.g. after extraction of the mRNA from the cells, transformation into DNA using reverse transcriptase, introduction of sticky ends, introduction into a cloning vector, and introduction of that vector into an appropriate host cell, e.g. a plasmid vector into a bacterium, such as a bacteriophage λ vector or a cosmid into *E. coli*, a yeast artificial into a yeast, such as *Saccaromyces cerevisiae*, a *Pichia-pastoris* vector into *Pichia pastoris*, or the like) or a DNA library (e.g. obtainable from selective digests of isolated DNA with restriction endonucleases, especially of type II, e.g. Alu I, Bam HI, Bgl I, Bst I, Eco RI, Eco RII, Fok I, Fnu DI, Hae II, Hae III, Hind II, Hind III, Hpa I, Msp I, Not I, Pst I, Sac I, Sal I, Sau 3A, Sma I, Taq I, Xho I, Xma I or as mentioned in the examples; if necessary, filling up recessed termini with Klenow fragment of *E. coli* DNA polymerase I, then ligating, e.g. with bacteriophage T4 DNA ligase, into a bacteriophage λ or cosmid vector for expression in *E. coli* or into a yeast artificial chromosome vector for expression in yeast) of the genomic DNA of the microorganism from which the enzyme of the invention can be isolated is then screened by stringent hybridization for matching polynucleotides (for appropriate conditions for stringent hybridisation see, for example, Sambrook et al., loc. cit., chapter 9) using (radioactive or fluorescence labeled) probes deduced from the known peptide fragments based on the genetic code which are produced according to standard procedures (fully degenerate, partially degenerate or using "guessmers"), which polynucleotides can then be isolated (e.g. from agar gels or the like) and sequenced. Longer nucleotides can be separated e.g. using pulsed field electrophoresis.

Hybridization is done using standard procedures, if necessary removing possible disturbing non-coding sequences, e.g. by PCR amplifying only the desired sequence parts or by endonuclease digestion, e.g. using dot blots of colonies of microorganisms from the DNA library. The positive clones can then be isolated.

The sequencing is done using standard procedures, e.g. the Maxam-Gilbert or the Sanger method.

If necessary, by combination of overlapping partial sequences the complete sequence coding for an enzyme of the invention (or one subunit thereof, if more than one polypeptide form the complete enzyme) can be determined.

From this sequence, the corresponding amino acid sequence of the enzyme is (or, if more than one polypeptide forms it, the subunits thereof, the amino acid sequences are) easily determined, using the genetic code.

In another approach, the full amino acid sequence of the isolated biocatalyst according to the invention can be determined (e.g. by different endopeptidase digests and matching of overlapping sequenced partial peptides) and a DNA coding the protein can be produced synthetically. It is also very easily possible to screen a suitable DNA library in a host, e.g. *E. coli*, for expression of temperature resistant alcohol dehydrogenase activity to obtain a transformed clone expressing the biocatalyst. Still another method makes use of antibodies against an enzyme of the invention that can be obtained using standard procedures (up to and including the production of monoclonal antibodies obtained from myelomas obtained according to standard procedures) in order to isolate the ribosomes carrying the mRNA coding for the enzyme, transforming it into the corresponding DNA (e.g. with reverse transcriptase) and sequencing or genetically engineering the resulting enzyme.

The nucleic acid according to the invention is preferably present in isolated form or in recombinant form (then also in a microorganism, see below).

The nucleic acids according to the invention also comprise modified (especially recombinant, but also naturally occurring) nucleic acids where, when compared with the form sequenced as described above, one or more nucleic acids are deleted, inserted, exchanged or added terminally, as long as the polypeptide or polypeptides for which they code still display alcohol dehydrogenase activity, especially according to the test method with 1-phenylethanol or acetophenone as described in the Examples.

Terminal additions may comprise the addition of sequences for vectors or host nucleic acids into which the coding sequence may be combined.

More preferably, the modified nucleic acids are modified such as to code for a biocatalyst with alcohol dehydrogenase activity, obtained by recombinant technology (resulting in a recombinant nucleic acid) or alternatively from natural sources, where the amino acid sequence of the biocatalyst comprises deletions, insertions, terminal additions or exchanges (especially conservative exchanges, e.g. of lipophilic against lipophilic, basic against basic, acidic against acidic, polar against polar amino acids, or the like) of amino acids (preferably of up to 20, in case of terminal additions up to 1000; more preferably of up to 5, in case of terminal additions of up to 200 amino acids, respectively), or any combination of such changes, when compared to the sequence of the enzyme as purified in the examples or possible different subunits thereof, as long as the basic activity (alcohol dehydrogenase activity, especially with the substrates (preferably 1-phenylethanol or acetophenone) and co-substrates mentioned in the examples) is still present, especially in connection with one or more of the additional advantageous properties mentioned for a biocatalyst according to the invention.

Most preferably, the modified nucleic acids contain 1 to 50, more preferably 1 to 12, additional nucleotides by insertion (especially additions yielding no frame shift), 1 to 50, more preferably 1 to 12 changes in nucleic acids, preferably resulting in conservative amino acid changes, and/or 1 to 50, more preferably 1 to 12, deletions of nucleotides, especially without frame shift.

The invention also relates to probes, especially in radiolabelled or fluorescence labelled form, that are hybridizable under stringent conditions to genomic or cDNA or other nucleic acids coding and that code for the sequences of the six partial amino acid sequences given as SEQ ID NO: 1 to SEQ ID NO: 6, or for parts thereof, said probes preferably having a length of 6 to 24, more preferably of 12 to 21 nucleotides.

The embodiment of the invention relating to microorganisms transformed with a nucleic acid coding for such a biocatalyst with alcohol dehydrogenase activity preferably relates to microorganisms appropriate for expressing the gene, but also those that comprise the nucleic acid for pure conservation or replication purposes.

Appropriate microorganisms are especially viruses, bacteriophages or especially host cells, for example, bacteria, e.g. *E. coli*, single cell fungi, such as yeasts, e.g. *Pichia pastoris, Schizosaccharomyces pombe* or *Saccharomyces cerevisiae*, or plant cells.

The microorganisms, especially host cells, can be transformed with nucleic acids as such that code for an enzyme of the invention; however, usually they are transformed with suitable vectors, e.g. plasmids, cosmids, yeast artificial chromosome or the like, which may comprise partial sequences (e.g. useful in sequence determination) or total sequences for the enzyme (e.g. useful in the expression of the enzyme).

Transformation of host cells is made according to standard procedures known in the art and appropriate for the respective host cells, e.g. according to the calcium chloride method, by electroporation, transformation after spheroblast formation into fungi, transformation with polyethylene glycol, transformation with lithium chloride, or the like. Virus or the like are modified by introduction of the sequences comprising the coding sequences for the enzyme of the invention.

Especially, the invention relates to the use of the microorganisms, especially host cells, in the production of said biocatalyst with alcohol dehydrogenase activity.

Expression systems suitable for production of an enzyme of the invention are especially phage-based expression systems in bacteria, e.g. bacteriophage λ or cosmids for *E. coli* as host, yeast artificial chromosomes for expression in *Saccharomyces cerevisiae*, the *Pichia pastoris* expression system used for expression in *Pichia pastoris*, expression systems in *Schizosaccaromyces pombe*, the baculovirus expression system or the like. In each of these systems, the nucleotide sequences coding for an enzyme of the invention can be expressed, either as such or with additional N- or C-terminal sequences, e.g. such that allow for direct export of the resulting polypeptide outside the expressing cells. These extra sequences, if disturbing the activity or otherwise not desired, can then be cleaved off using appropriate endoproteases known in the art.

PREFERRED EMBODIMENTS OF THE INVENTION

Preferred embodiments of the invention are represented in the dependent claims, where in each case more general terms can be replaced with more specific terms provided in the definitions above, independently of other terms, in order to define still more preferred embodiments.

The invention relates in particular to the use of/process using the enzyme of the invention, and especially to the enzyme described in the Examples.

The following examples are illustrative, however, do not limit the scope of the present invention.

EXAMPLES

Example 1

Cultivation of *Rhodococcus ruber* DSM 14855

The Gram-positive bacterium *Rhodococcus ruber* DSM 14855 is grown under aerobic conditions in baffled Erlenmeyer flasks at 30° C. and 130 rpm using a complex medium containing yeast extract, peptone, glucose and mineral salts (10 g/l yeast extract (OXOID CM129, OXOID Ltd., Hampshire, England), 10 g/l peptone, 2 g/l NaCl, 0.15 g/l $MgSO_4 \cdot 7H_2O$, 1.3 g/l $NaH_2PO_4$, 4.4 g/l $K_2HPO_4$) for three days. Cell growth is followed by determination of the optical density via absorption at 546 nm, see Table 1. After a centrifugation (2000 g, 20 min), the pellet is taken up in Tris-HCl buffer pH 7.5 (50 mM), shock-frozen in liquid nitrogen and lyophilised.

The cells produce several $NAD^+$/NADH-dependent sec-alcohol dehydrogenases without any induction. The highest sec-alcohol dehydrogenase activity is displayed during the late exponential and early stationary phase of the growth curve (see table 1). The activity is measured as the ability of the cells to oxidise 1-phenylethanol or the ability to reduce acetophenone.

For this test, whole lyophilised cells of Rhodococcus ruber DSM 14855 (20 mg) are rehydrated in phosphate buffer (0.5 ml, 50 mM, pH 7.5) for 30 min. Activity is measured by adding acetophenone (0.27 mmol) and 2-propanol (0.4 ml). The mixture is shaken at 24° C., 130 rpm in eppendorf vials for 2.5 h. The reaction is quenched by addition of ethyl acetate (1 ml) and centrifugation. The conversion is determined by GC (Varian 3800, FID) on an achiral column (HP-1301, 30 m×0.25 mm×0.25 µm; $N_2$). Temperature program for rac-1-phenylethanol/acetophenone: start temperature 80° C.—hold 2 min—10° C./min—until 130° C.—hold 2 min. The conversion is calculated from calibration curves. For the inverse test, 1-phenylethanol is oxidised in the presence of acetone as co-substrate.

TABLE 1 sec-Alcohol dehydrogenase activity versus growth curve for Rhodococcus ruber DSM 14855

| Relative Cell Density (OD 546 nm) | Time of growth (h) | Sec-alcohol dehydrogenase activity (%) |
| --- | --- | --- |
| 3.7 | 0 | 35 |
| 2.8 | 2 | 34 |
| 2.7 | 4 | 37 |
| 3.4 | 6 | 59 |
| 3.6 | 8 | 65 |
| 4.8 | 10 | 81 |
| 6.5 | 12 | 86 |
| 7.2 | 14 | 78 |
| 9.1 | 16 | 81 |
| 10.1 | 18 | 84 |
| 11.0 | 20 | 100 |
| 12.4 | 22 | 66 |
| 15.9 | 24 | 54 |
| 21.0 | 26 | 42 |
| 27.2 | 28 | 46 |
| 34.4 | 30 | 34 |
| 39.7 | 32 | 43 |
| 38.1 | 34 | 34 |

Example 2

Purification of a sec-Alcohol dehydrogenase 'ADH-A' from Rhodococcus ruber DSM 14855 a) Cell Disruption

Bearing in mind that the sec-alcohol dehydrogenase might be a membrane-associated or even membrane-bound protein, cell disruption using a Vibrogen cell mill (glass beads, diameter 0.25 mm, Vibrogen Zellmühle, E. Bühler, Typ VI-4; Braun Biotech Int., Melsungen, Germany) is used and optimised in order to obtain the majority of the activity in the cell-free lysate and not in the cell debris fraction. This results in an exceptionally long and rough procedure of 7 shaking cycles of 2 min agitation/5 min cooling each. The enzyme shows high stability against this strong mechanical treatment. The buffer used for cell disruption is 10 mM Tris-HCl buffer, pH 7.5.

TABLE 2

Optimization of the cell disruption by increasing number of shaking cycles

| Relative Activity [%] | 48 | 60 | 71 | 85 | 82 | 97 | 100 | 93 | 82 |
| --- | --- | --- | --- | --- | --- | --- | --- | --- | --- |
| Number of shaking cycles | 1 | 2 | 3 | 4 | 5 | 6 | 7 | 8 | 9 | b) Pre-Treatment with DEAE-Cellulose:

Due to the harsh breaking of the cells, several undesired materials such as carotenoids, lipids and surface-active components are released from the cells beyond the sec-alcohol dehydrogenase activity. Those components lead to immense filtration problems and are thus removed by treatment with DEAE (Diethylaminoethan)-Cellulose (Sigma) in a batch procedure. All sec-alcohol dehydrogenase activity is bound onto the matrix in 10 mM Tris-HCl buffer pH 7.5 and can be eluted by addition of 0.5 M NaCl to the buffer.

c) Purification Steps

The purification of the sec-alcohol dehydrogenase by FPLC (Fast Protein Liquid Chromatography)-methods starts with the cell-free lysate after pre-treatment with DEAE-Cellulose.

(i) Hydrophobic Interaction Chromatography

The first protein purification step is a Hydrophobic Interaction Chromatography using Phenyl Sepharose High Performance material ((Amersham Pharmacia Biotech AB, Uppsala, Sweden). During sample preparation precipitation occurs by adding $(NH_4)_2SO_4$), and solids are removed since they do not contain any sec-alcohol dehydrogenase activity. With addition of $(NH_4)_2SO_4$ as salting-out medium to the equilibration buffer and a stepwise gradient, the different hydrophobicities of proteins enable a first separation of enzymes. Two $NAD^+/NADH$ dependent sec-alcohol dehydrogenase activities are found, but just one fraction, arbitrarily called sec-'ADH-A' (standing for sec-alcohol dehydrogenase+'acetone') shows stability against the co-substrates acetone/2-propanol. The second activity, called $B_1$, is significantly less stable and is thus not further investigated.

Details of step (i): Column length 75 mm, diameter 16 mm. Eluent: A: B+1 M $(NH_4)_2SO_4$; B=10 mM Tris-HCl buffer pH 7.5.

Application volume: 3 times 46 ml are administered (3 separate runs).

Elution: first 70 ml A, then 47.5 ml 50% A+50% B, then 47.5 ml 25% A+75% B, then linear gradient during 47.5 ml from 25% A+75% B to 100% B and further elution with this eluent. Flow rate 4 ml/min.

Activity of $B_1$ is found between 70 and 118 ml. Activity of sec-'ADH-A' is found between 220 and 236 ml elution volume. The latter (3×16 ml after 3 runs, a total of 48 ml) is used for further purification.

(ii) Ion Exchange Chromatography

The complete fraction (46 ml) containing sec-'ADH-A' is further purified by Ion Exchange Chromatography using the anion exchanging column UNO Q6 (BioRad). By running an optimised stepwise gradient using chloride as counter ion in the elution buffer, the sec-alcohol dehydrogenase activity is separated again into two NAD⁺/NADH dependent fractions, whereof again one is identified as sec-ADH A. The second sec-ADH $B_2$ is significantly less stable and thus is not further investigated.

Details of step (ii) Column length 53 mm, diameter 12 mm.
Elution buffer: A 10 mM Tris-HCl-buffer pH 7.5; B: A+1.5 M NaCl ("100% NaCl).

Gradient: First elution with 62 ml of A, then with 67 ml of 82.75% A+17.5% B, then with 28 ml of 50% A+50% B, finally with pure B. Flow rate 4 ml/min.

Activity of $B_3$ is found between 68 and 82 ml. Activity of sec-'ADH-A' is found between 131 and 137 ml elution volume. The latter (6 ml) is used for further purification.

(iii) Affinity Chromatography

The third step in protein purification of the resulting 6 ml from step (iii) is carried out on an innovative material, Blue Sepharose CI-6B [see Shaw et al., Biochem. J. 187, 181 (1996)], containing a dye, Cibacron Blue F3G-A, specific for enzymes requiring adenylyl-containing cofactors (such as NAD⁺/NADP⁺) (Amersham Pharmacia Biotech AB, Uppsala, Sweden).

In contrast to theory, sec-'ADH-A' does not bind on the matrix but elutes right after the void volume, regardless of the conditions used. But at linear increased salt concentration, another sec-ADH is found and is identified again as NAD⁺/NADH dependent sec-alcohol dehydrogenase $B_3$, which is significantly less stable and thus not further investigated.

Details of step (iii): Column length 60 mm, diameter 16 mm.
Eluent: Buffer A: 10 mM Bis-tris-HCl buffer pH 6.0; Buffer B: A+1 M NaCl.
Gradient: First 31 ml of buffer A, then linear gradient from 100% buffer A to 100% buffer B.

Flow Rate 4 ml/min.

Activity of alcohol dehydrogenase $B_3$ is found between 44 and 68 ml. Activity of sec-'ADH-A' is found between 7 and 23 ml elution volume. The latter is concentrated up on Centriplus YM-10, cut-off 10 kDa (regenerated cellulose with 10 kDa exclusion size) from Millipore (Millipore GmbH, Vienna, AT)/Amicon to a final volume of 2 ml.

(iv) 2.3.4 Size Exclusion

Size exclusion using this Superdex 200 column (Amersham Pharmacia Biotech AB, Uppsala, Sweden) leads to final purification, the only sec-alcohol dehydrogenase activity detected is Sec-ADH A. 10 runs with 0.2 ml each of the resulting 2 ml in step (ii) are used.

As the column is calibrated with several standard proteins, namely yeast alcohol dehydrogenase (150 kDa), Bovine Serum Albumin (67 kDa), ovalbumin (43 kDa), chymotrypsinogen (25 kDa) and blue dextran (2 kDa), the molecular weight of the native enzyme is determined as approximately 62 kDa.

Details for step (iv): Column length 310 mm, diameter 10 mm.
Eluent: 50 mM $NaH_2PO_4$, 0.15 M NaCl, pH 7.0
Flow Rate 4 ml/min.

10 times 1 ml of fractions containing the activity of sec-'ADH-A' are obtained (after about 13 ml of elution). The molecular weight is determined based on the peak concentration of the ADH-A activity.

Summary of the Purification Protocol:

Following this protocol, the sec-alcohol dehydrogenase 'ADH-A' is purified reproducibly. The small overall recovery is explained by a major loss of activity during desalting procedures and buffer exchange via dialysis and during concentration to a small volume before applying it to the size-exclusion column. For this reason, the majority of biochemical characterizations are carried out with semipure enzyme after the dye chromatography, where no other sec alcohol dehydrogenase activity is left.

In addition, the "low" yield is attributable to the fact that in the cell extract at the beginning other alcohol dehydrogenases that are removed during the later procedure (e.g. $B_1$, $B_2$ and $B_3$) contribute to the dehydrogenase activity.

In the following table, 1 U=1 μMol/min.

The activity is determined by oxidation of 1-phenylethanol (6.6 μM) and addition of 10 mM NAD⁺ (testing conditions: 30° C., 10 μM Tris-buffer, pH 7.5, 10 min, conversion by GC-analysis). Protein amounts are measured by the method of Bradford (Coomassie Blue Protein Assay) at 595 nm using a BioRad Protein Assay:

TABLE 3

Purification Table

| Step | V [ml] | Protein [mg/ml] | Tot. Protein [mg] | Activity [Units/ml] | Tot. Act. [Units] | Spec. Act [Units/mg] | f | Yield [%] |
| --- | --- | --- | --- | --- | --- | --- | --- | --- |
| crude extract | 122 | 8.2 | 1000 | 0.13 | 16 | 0.016 | 1 | 100 |
| DEAE Cell. | 139 | 3.4 | 472 | 0.27 | 37 | 0.078 | 5 | 232 |
| Ph. Sepharose HP | 48 | 1.4 | 67 | 0.17 | 8 | 0.123 | 8 | 52 |
| UNO Q6* | 6 | 0.7 | 4.2 | 0.47 | 3 | 0.672 | 43 | 18 |
| Blue Sepharose | 16 | 0.03 | 0.5 | 0.07 | 1 | 2.2 | 138 | 7 |
| Superdex 200* | 10 | 0.0075 | 0.075 | 0.13 | 1.3 | 17.5 | 1100 | 8 |

Example 3

Purification Control and Molecular Weight Determination by Gel Electrophoresis

The progress of the protein purification is controlled by native as well as by SDS-polyacrylamide gel electrophoresis (PAGE). For both methods, the protein fractions are subjected to a Laemmli SDS-PAGE system using a MINI-PROTEAN II dual slab cell (BioRad).

a) Native Gel Electrophoresis

Active fractions are treated with non-denaturing sample buffer and loaded on a polyacrylamide gel (12%) without SDS. The gel is run at 4° C. at 150 V with running buffer containing 15 g/l Tris and 72 g/l Glycine. The method for visualization of sec-alcohol dehydrogenases in polyacrylamide gels was first reported by Grell et al. [see Science 149, 80 (1965)] and is based on a staining solution [see Dodgson et al., Biochem. J. 187, 703 (1996)] mixed from aqueous 4 mM 2-octanol (or any aliphatic, long-chained sec-alcohol accepted as substrate) and 100 mM Tris-HCl buffer pH 8.5 containing 3 g/l NAD$^+$, 0.1 g/l phenazinemethosulphate (N-methyldibenzopyrazine ethylsulfate salt) and 1 g/l nitro blue tetrazolium. Purple spots of the reduced formazane are usually visible within 30 min of incubation and display the presence of a sec-alcohol dehydrogenase. For result see FIG. 1.

There are at least seven different sec-alcohol dehydrogenases present in the microorganism, of which sec-alcohol dehydrogenase 'ADH-A' can be separated properly during the purification protocol.

b) SDS Polyacrylamide Gel Electrophoresis

In this case, the same protein samples used for native electrophoresis are denaturated with sample buffer (SDS reducing buffer, BioRad) and administered to a SDS-polyacrylamide gel (12%) subsequently run at 200V at room temperature in the same running buffer with addition of 3 g/l SDS. After the run, staining is carried out with Coomassie Brilliant Blue. The molecular weight is determined in comparison to a low molecular weight range SigmaMarker as protein standard containing albumin (66 kDa), ovalbumin (45 kDa), glyceraldehyde-3-phosphate dehydrogenase (36 kDa), carbonic anhydrase (29 kDa), trypsinogen (24 kDa), trypsin inhibitor (20 kDa), α-lactalbumin (14.2 kDa) and aprotinin (6.5 kDa). The result is a single band after the size exclusion corresponding to 38 kDa.

Example 4

Characterisation of Sec-alcohol Dehydrogenase "ADH-A" from *Rhodococcus ruber* DSM 14855 a) Determination of Molecular Weight:

The molecular weight is determined by running SDS-polyacrylamide gel electrophoresis and in parallel by a size exclusion column calibrated with standard proteins. The elution of the purified protein on Superdex 200 indicates a molecular mass for the native enzyme of about 62 kDa. In contrast, the SDS-PAGE procedure results in a single band at 38 kDa. This discrepancy may be explained by the structure of the protein, as either (i) long thin proteins elute generally earlier than globular proteins or (ii) a dimer may be present. Due to the unsymmetric peak form of the protein in relation to the standards, the determination of the peak maximum limits the accuracy of molecular weight calculations.

b) pH-Optimum

The measurements are carried out in 25 mM Tris-maleate pH 6.0-9.0 and 50 mM NaH$_2$PO$_4$ pH 10.0-11.0, and the activity is determined via conversion of 1-phenylethanol or acetophenone (6.6 mM) by addition of 10 mM NAD$^+$ or NADH, respectively. The reaction time is 10 min at 50° C. The present enzyme displays activity over a broad range of pH values (see Table 4). The pH-optimum is different for the two possible reactions. While the enantioselective (ee>99%) reduction of ketones prefers a pH of 6.5-7.5, the oxidation of sec-alcohols is enhanced in more basic conditions and is very efficient over an extremely broad pH-range. The selectivity of the oxidation does not change when the pH is raised, i.e. ee=>98% at pH 9.0. Routinely, all reactions are conducted at pH 7.5 for both oxidation and reduction to minimize buffer exchange procedures.

TABLE 4 pH-optimum

| Relative Activity [%] | Oxidation | 31 | 46 | 51 | 67 | 100 | 82 | 78 |
|---|---|---|---|---|---|---|---|---|
| | Reduction | 70 | 100 | 85 | 78 | 56 | 19 | 15 |
| PH | | 6 | 6.5 | 7 | 8 | 9 | 10 | 11 | c) Temperature Optimum

The effect of temperature on the sec-alcohol dehydrogenase 'ADH-A' is measured in 10 mM Tris-HCl buffer pH 7.5, 1-phenylethanol or acetophenone (6.6 mM) are used as substrates in presence of 10 mM NAD+/NADH, respectively. Substrate and enzyme are incubated for 5 min using a thermostated shaker at a set temperature. Then the reaction is started at this temperature by addition of NAD+/NADH and the reaction is carried out for 10 min. Surprisingly, the sec-alcohol dehydrogenase 'ADH-A' shows maximum of activity within the range of 45 to 65° C., an exceptionally high value (See Table 5). Inactivation occurs quite suddenly at 70° C.

TABLE 5

Temperature Optimum

| Relative Activity [%] | Oxidation | 22 | 39 | 70 | 66 | 98 | 100 | 96 | 2 |
|---|---|---|---|---|---|---|---|---|---|
| | Reduction | 37 | 67 | 57 | 51 | 72 | 100 | 94 | 3 |
| Temperature [° C.] | | 12 | 20 | 29 | 38 | 46 | 54 | 64 | 70 | d) Temperature Stability

For the determination of enzyme stability at different temperatures, oxidation as well as reduction are performed as described before in 10 mM Tris-HCl buffer pH 7.5 and within a temperature range from 25 to 50° C. After incubation of the enzyme solution at 50° C., the reaction is started by addition of the corresponding cofactor and is run for 10 min. Again (see Table 6), the sec-alcohol dehydrogenase 'ADH-A' displays an exceptional thermo-stability for a protein from *Rhodococcus ruber* DSM 14855, which is not known as a thermophile. The loss of activity after 24 hours is rather small for both the oxidation and reduction system, which indicates an enormous stability of the protein. Due to this property, a wide scope of industrial applications can be anticipated.

TABLE 6

Temperature stability

| Relative Activity [%] | Oxidation 50° C. | 100 | 94 | 77 | 8 |
|---|---|---|---|---|---|
| | Reduction 50° C. | 100 | 78 | 79 | 5 |
| | Oxidation 30° C. | 100 | 91 | 91 | 12 |
| | Reduction 30° C. | 100 | 75 | 73 | 6 |
| Time [h] | | 0 | 8 | 24 | 48 | d) Presence of Zinc

ICP-MS analysis shows the presence of Zn$^{2+}$ in the purified enzyme preparation (see Hemmers, B., et al., J. Biol. Chem. 275, 35786-35791 (2000), for the method). Whether this is required for catalytic activity and forms a true component of the enzyme is not determined at present. As the enzyme is both active in the presence of complex forming agents such as

Example 5

Coupled Enzymatic Reduction/Oxidation System

Despite impressive progress in the regeneration of nicotinamide cofactors on the lab-scale using the 'coupled-enzyme method' [see, e.g., Hummel, Trends Biotechnol. 17, 487 (1999) or Chenault et al., Appl. Biochem. Biotechnol. 14, 147 (1987)], purified redox enzymes are not ideally suited for industrial applications due to their limited operational lifetime. In contrast, the so-called 'coupled-substrate-approach' is restricted due to the limited tolerance of most ADH's towards elevated (co)substrate concentrations [see Faber, Biotransformations in Organic Chemistry, 4$^{th}$ edition, Springer, Heidelberg 2000, pp. 177-183]. In contrast, ADH-A is ideally suited for this simple protocol, which is fully commensurate with the requirements of Industrial applications. The purified enzyme is exceptionally stable towards acetone or 2-propanol in up to 10% v/v concentration for cofactor-recycling in oxidation and reduction, respectively. In addition, excellent storage stability (no loss of activity after 14 days at +4° C., or after several months at −80° C., or in lyophilised form) makes this enzyme a prime candidate for large-scale applications. In particular, more lipophilic substrates are rapidly transformed due to their enhanced solubility in aqueous/organic systems (as compared to pure aqueous systems).

The following Tables show the reduction of various ketone substrates (Table 7) and the oxidation of various sec-alcohol substrates (Table 8).

The steric preference of the reduction follows the Prelog rules. In the case of oxidation, that enantiomer is oxidised that would be formed during reduction of the respective ketone.

TABLE 7

Reduction Of 2-methyl-2-hepten-6-one by partially purified enzyme (after Hydrophobic Interaction Chromatography), using 2-propanol as co-substrate (10 µM substrate, 10 mM NADH, 30° C.; 100% relative activity. 0.44 µmol conversion/mg protein):

| 2-Propanol (% v/v) | Relative Activity (%) | ee |
|---|---|---|
| 0 | 15 | 90 |
| 5 | 31 | >99 |
| 10 | 34 | >99 |
| 20 | 37 | >99 |
| 30 | 44 | >99 |
| 40 | 51 | >99 |
| 50 | 61 | >99 |
| 60 | 76 | >99 |
| 70 | 100 | >99 |
| 80 | 95 | >99 |
| 90 | 25 | >99 |

TABLE 8

Oxidation of 2-octanol by partially purified enzyme (after Hydrophobic Interaction Chromatography) using acetone as co-substrate (10 µM substrate, 10 mM NAD$^+$, 30° C., 12 h; 100% rel. act. = 13 µmol conversion/mg protein):

| Acetone (% v/v) | Relative Activity (%) | ee | E* |
|---|---|---|---|
| 0 | 17 | 17 | 10 |
| 5 | 98 | 81 | 2 |
| 10 | 100 | 97 | 3 |
| 20 | 89 | >99 | 10 |
| 30 | 88 | >99 | 18 |
| 40 | 88 | >99 | 58 |
| 50 | 97 | 94 | 100 |
| 60 | 62 | 36 | >100 |
| 70 | 34 | 14 | >100 |
| 80 | 15 | 5 | >100 |
| 90 | 17 | 3 | >100 |

*E is the Enantiomeric ratio (see Chen., C.-S., et al., J. Am. Chem. Soc. 104, 7294-99 (1982) (quotient of the reaction velocities of the isomers)

Analogously, the following reactions can take place:

Reduction of: 2-heptanone, 2-octanone, 2-nonanone, 2-decanone, 1-cyclohexylethanone, 1(naphtha-2-yl)ethanone, oct-3-en-2-one (leading to the S-enantiomers in more than 97% ee).

Oxidation of: rac-$(CH_3)_2C$=CH—$(CH_2)_2$—CHOH—$CH_3$, rac-n-$C_6H_{13}$—CHOH—$CH_3$, rac-4-phenyl-2-butanol, rac-$(E)_3$-octen-2-on, cyclopentanol, rac-(1-(2-naphthyl)ethanol, rac-1-phenyl-1ethanol.

Example 6

Determination of Parts of the Protein Sequence of "ADH-A"

Using a MS/MS de novo-sequencing protocol after tryptic digestion (see Lehmann, W. D., Massenspektroskopie in der Biochemie (=Mass Spectroscopy in Biochemistry), Spektrum Akad. Verlag, pp. 274-293, 1996 (ISBN 3-86025-094-9)) for the purified "ADH-A" enzyme obtained according to example 2, the following results are obtained.

4 tryptic peptides are sequenced completely (SEQ ID NO: 1-4), one of them also being found as part of a somewhat larger peptide (SEQ ID NO: 5) with possibly modified N-terminus, and a tryptic peptide with an ambiguity in the N-terminal sequence is found (SEQ ID NO: 6), where [L/I] is leucine or isoleucine and X is an unidentified amino acid:

| Sequence | SEQ ID NO: |
|---|---|
| EVGADAAAR | 1 |
| TD[L/I]FEVVA[L/I]AR | 2 |
| SGAGAADA[L/I]R | 3 |
| V[L/I]AVD[L/I]DDDR | 4 |
| V[L/I]AVDXDDDXRX | 5 |

-continued

| Sequence | SEQ ID NO: |
|---|---|
| [TD/DT] [L/I]MEVVA[L/I]AR | 6 (either with TD in the beginning or with DT in the beginning) |

Example 7

Obtaining of Nucleotide Sequences Corresponding to the Enzyme "ADH-A"

Taking one of the peptide sequences given above in Example 6 or two or more thereof, especially SEQ ID NO: 1, the corresponding (fully degenerate, then preferably only the nucleotides corresponding to 3 to 6 of the amino acids given are used; partially degenerate, then also longer nucleotides can be synthesized, with non-specific nucleotides at positions of; or "guessmers" that have only one specific sequence) nucleotide sequence corresponding to (sense sequence) or complementary (antisense) to the nucleotide sequence of the corresponding mRNA, based on the standard genetic code, is synthesized (e.g. according to Narang, Tetrahedron 39, 3 (1986) or Itakura et al, Annu. Rev. Biochem. 53, 323 (1984); or using standard oligonucleotide synthesizers). For determination of useful oligonucleotides, their purification and use and the preparation of radio-labelled probes, the methods described by Sambrook et al., Molecular Cloning—a Laboratory Manual, Cold Spring Harbor Laboratory Press, pages 11.1 to 11.44 are be used. The labelled oligonucleotide or oligonucleotides are then hybridised (for conditions see Sambrook et al., loc. cit, pages 11.45 to 11.61) to cDNA libraries (obtained according to Sambrook et al., loc. cit. pages 8.1 to 8.86). After identification of colonies with positive signals, these are grown and the vectors containing the hybridisable cDNA are isolated. The DNA is then sequenced according to standard methods (e.g. as shown in Sambrook et al., loc. cit., pages 13.1 to 13.103).

In one example, polymerase chain reaction is used for the preparation of the cDNA (see Lee, C. C., et al., Science 239(4845), 1288-91 (1988)).

The sequences between a start and a termination codon include the sequence(s) coding for the peptide backbone(s) of a part or the whole enzyme "ADH-A" or homologues displaying similar activity.

Example 8

Isolation and characterization of the polynucleotide coding for ADH-A and Determination of the Corresponding Amino Acid Sequence A) Isolation of Chromosomal DNA from *Rhodococcus ruber* DSM 14855

A *Rhodococcus ruber* DSM 44541 preculture is cultivated in 500 ml standard complex medium (10 g Yeast Extract, Oxoid L21; 10 g Bacteriological Peptone, Oxoid L 37; 10 g glucose, Fluka 49150; 2 g NaCl, Roth 9265.1; 0.15 g MgSO$_4$2O, Fluka 63140; 18 g Agar, Oxoid L11; 1.3 g NaH$_2$PO$_4$, Fluka 71496; 4.4 g K$_2$HPO$_4$, Merck 5101; all amounts per litre) overnight at 30° C. and 130 rpm. The cell suspension is then centrifuged at 3900×g, washed with 50 ml 20% glycerol and pelleted at further time. 1 g of the cell pellet is resuspended with 3 ml TE25S-Puffer (25 mM Tris pH 8; 25 mM EDTA; 0.3M saccharose) and incubated with addition of lysozyme (Sigma L7651, final concentration 2 mg/ml) for 3 h at 37° C. After addition of 4 ml disintegration solution (10 ml 10% SDS; 6 g sodium-4-aminosalicylate, Sigma #A3505; 2.5 ml 2M Tris pH 8; 3 ml phenol; ad 50 ml distilled water, store under protection from light) inversion for 10 min at room temperature (RT) follows, and after the addition of 8 ml phenol/chloroform/isoamyl alcohol a further inversion is performed. After centrifugation at 3900×g the aqueous phase is decanted and is again complemented with phenol, precipitated by addition of 0.6 vol. propan-2-ol and 0.1 vol. 3M sodium-acetate and subsequently washed in 70% ethanol, dried and dissolved overnight at 4° C. in H$_2$O. After this, the DNA is incubated with addition of 40 μg/ml RNase A (Applichem, A3832) 1 h at 37° C. and, after that, further incubated with addition of 500 μg/ml proteinase K (Merck KGaA, #1.24568) 1 h at 37° C. After another addition of phenol (see above) and precipitation with propan-2-ol, the purified DNA is dissolved in an appropriate volume of H$_2$O.

B) Sequence Analysis and deduction of degenerate Primers

Various attempts to make use of classical cloning attempts failed to provide a success in obtaining the complete or at least partial sequence of the gene coding for an alcohol dehydrogenase according to the invention. Thus, both the sequence analysis of related alcohol dehydrogenases and the synthesis of degenerate primers on the basis of conserved regions as well as the deduction of degenerate primers (see below) on the basis of known internal peptide sequences of the alcohol dehydrogenase according to the invention (ADH-A), in both cases with subsequent PCR screening of the chromosomal DNA failed.

Apparently the high GC content of the gene that can be deduced from the sequence as finally recovered using a novel approach was responsible for the formation of stable or disturbing secondary structures that led to this problem.

After various fruitless attempt, surprisingly only a combination of primers that results from both approaches leads with the primers identified below to the identification of a partial sequence of the gene.

B1) Deduction of Degenerate Oligonucleotide Primers on the Basis of Known Internal Peptide Sequences of ADH-A Based on the peptide sequences

| | |
|---|---|
| VXAVDXDDDR | (SEQ ID NO: 49) |
| EVGADAAVKSGAGAAGAXR | (SEQ ID NO: 50) |
| XFEVVAXAR | (SEQ ID NO: 51) |
| XMEVVAXAR | (SEQ ID NO: 6) | where X in each case stands for leucine or isoleucine and which are identical to the peptides mentioned above and/or deduced from them and published sequences using a data bank, alcohol dehydrogenase sequences are identified that provide partial similarity to these peptides. The sequences taken into consideration for this purpose have the accession numbers NP_631415, ZP_00058234, BAA35108 and CAD36475.1 in or accessible via the NCBI databank. On the basis of these sequences, degenerate oligonucleotide primers are deduced from highly conserved regions identified in these sequences.

```
blockA-F1   5'-CGGAGCCGGGCCCNGGNSARRT-3'         SEQ ID NO: 7 blockB-F1   5'-CTACGAGCTGCCGCTGACNYTNGGNCA-3'    SEQ ID NO. 8 blockC-F1   5'-GTCGTCGTCTACGGCCCNTGGGGNTG-3'     SEQ ID NO: 9 blockC-F2   5'-GACAACGTCGTCGTCTACGGNCCNTGGGG-3'  SEQ ID NO: 10 blockE-F1   5'-GCACCGGCGGCCTNGGNCAYGTNG-3'       SEQ ID NO: 11 blockG-R1   5'-GCTGGTCGCCGACGAARTCNARNAC-3'      SEQ ID NO: 12 blockH-R1   5'-CATCAGCTCGGTGCGGSHNCCCCARTA-3'    SEQ ID NO: 13 blockH-R2   5'-GCCAGGTCGACGACCTCNRTNARYTC-3'     SEQ ID NO: 14 blockI-F1   5'-GGNCACGARGGNGTCGGNNNNGTCGC-3'     SEQ ID NO: 15 blockI-F2   5'-GGNCACGARGGNGTCGG-3'              SEQ ID NO: 16 blockI-F3   5'-CCNYTIACIYTIGGICA-3'              SEQ ID NO: 17 blockK-F1   5'-GTNTAYGGICCITGGGG-3'              SEQ ID NO: 18 blockK-F2   5'-CCNYTNACIGAYGCIGG-3'              SEQ ID NO: 19 blockK-R    5'-CCNGCRTCIGTIARIGG-3'              SEQ ID NO: 20 blockL-R    5'-CGNGTNCCCCARTAIGG-3'              SEQ ID NO: 21 blockM-F1   5'-ATGAAAGCCCTCCAGTACACCG-3'         SEQ ID NO: 22 blockM-F2   5'-ATGAARGCSCTSCARTACACS-3'          SEQ ID NO: 23 blockN-R1   5'-TCAGCCCGGGACGACCACC-3'            SEQ ID NO: 24 blockN-R2   5'-ANCCNGGNACNACNACNCC-3'            SEQ ID NO: 25
``` where I in each case is inosine.

The oligonucleotide primers are then used for a PCR screening using the isolated chromosomal DNA from *R. ruber* DSM 14855 (obtained as described under A) above).

B2) Deduction of Degenerate Primers on the Basis of Peptide Sequences from Native Alcohol Dehydrocenase A (ADH-A):

The following degenerate primers are used for a PCR screening based on the peptide partial sequences described in B1).

```
pepA-F1   GTSATCGCNGTCGAYCTSGACGACGAC    SEQ ID NO: 26 pepA-F2   GTCATHGCSGTCGACNTNGACGACGA     SEQ ID NO: 27 pepA-F3   GCNGTNGAYYTIGAYGAYGA           SEQ ID NO: 28 pepA-F4   GTCGATCTCGACGACGACCG           SEQ ID NO: 29 pepA-R1   GTCGTCGTCSAGRTCGACNGCGATSAC    SEQ ID NO: 30 pepA-R2   TCGTCGTCNANGTCGACSGCDATGAC     SEQ ID NO: 31 pepA-R3   TCRTCRTCIAIRTCIACIGC           SEQ ID NO: 32 pepA-R4   CGTCGTCGAGATCGACGGC            SEQ ID NO: 33 pepB1-F1  GARGTNGGCGCSGACGCSGCS          SEQ ID NO: 34 pepB2-F1  GGNGCSGGNGCSGCSGACGCSATC       SEQ ID NO: 35

PepB1-F2  GARGTNGGNGCNGAYGCNGC           SEQ ID NO: 36 pepB1-R1  GCSGCGTCSGCGCCNACRTC           SEQ ID NO: 37 pepB1-R2  GCNGCRTCNGCNCCNACYTC           SEQ ID NO: 38 pepB2-R1  GATSGCGTCSGCSGCNCCSGCNGG       SEQ ID NO: 39 pepC-R1   CGSGCSAGGTCSACSACGTCCAT        SEQ ID NO: 40 pepC1-F   GGNGCNGGNGCNGCNGAYGC           SEQ ID NO: 41 pepC1-R1  GCRTCNGCNGCNCCNGCNCC           SEQ ID NO: 42 pepC1-R2  GCCGCCCCGGCGCC                 SEQ ID NO: 43 pepD-R    CKNGCNARIGCIACIAC              SEQ ID NO: 44
(I is inosine)
```

B3) PCR Screening with the Help of Degenerate Primers:

The primers mentioned under B1) and B2) are used in all possible combinations in a PCR.

PCR conditions:

| Cycles | Time   | Temperature |
|--------|--------|-------------|
| 1      | 15 min | 95° C.      |
|        | 30 sec | 95° C.      |
| 30     | 30 sec | 50° C.      |
|        | 30 sec | 72° C.      |
| 1      | 7 min  | 72° C.      |

For this purpose, the HotStar-Taq Master-Mix (Qiagen, Hilden, Germany) is used in accordance with the instructions provided by the manufacturer.

However, using the standard conditions, no amplificates are found. Only by elongation of the time allowed for annealing to a total of 2 min, an about 350 bp fragment can be generated with the primer pair blockC_F2-pepA-R1 (SEQ ID NO: 10 and SEQ ID NO: 30).

Surprisingly only a combination of these primers leads to the desired result.

After sequencing of the partial fragment, on the basis of these data specific "nested primers" are manufactured for the PCR screening of a DNA bank from *Rhodococcus ruber* DSM 14855.

```
RS_1-F1        CCTGCGCGCGCGGCCGGGAG      SEQ ID NO: 45
               AACTAC

Asb_030730_R   CAGGATCTGGATGCCGACGT      SEQ ID NO: 46
               GGCCGAG
```

C) Production of a DNA bank from *Rhodococcus ruber* DSM 14855

For establishing a DNA bank, the Expand I-cosmid vector with an insert capacity of 9-16 kb (Roche Diagnostics GmbH, Mannheim, Germany) is used. The chromosomal DNA from *R. ruber* DSM 14855 described under A) is restriction digested with AluI (NEB Inc., Beverly, USA) as follows:

3 μg chromosomal DNA from *R. ruber* DSM 14855
1.5 U AluI
2 μl restriction buffer
ad 20 μl H$_2$O
Incubation 4 min, 37° C.

The restriction is stopped by addition of phenol, the DNA is precipitated and dissolved in distilled H$_2$O. The subsequent ligation is achieved with the SmaI-restricted and dephosphorylated vector arms of the Expand I-vector Composition of the Incubation Mixture:
100 ng Expand I-Vektor
450 ng AluI-restricted *R. rubber* DSM 14855 DNA
2 μl ligase buffer
0.5 μl ligase (NEB Inc., Beverly, USA)
ad 20 μl H2O
Incubation at 16° C., overnight The in vitro packaging and transformation of *Escherichia coli* DH5α is performed in accordance with the manufacturer's instructions (Expand-Cloning Kit; Roche Diagnostics GmbH, Mannheim). A total of about 2500 clones is generated and archived in a 384 hole microtiter plate (MTP) format in a total of 6 MTPs in LB-liquid medium. A restriction analysis displayed for 10 clones selected at random the expected insert size from 9-16 kb.

D) Identification of a Cosmid Clone Including the Partial Sequence by Means of GRID-PCR Screening For identification of the clone with the complete ADH-A sequence a grid PCR screening employing the nested primer mentioned using the "nested primers" mentioned under B2), RS1_F1 und Asb_030730_R is performed. For this purpose, the clones of the 6 MTPs obtained under C) are replicated on LB solid medium and the cosmid DNA of the cells of each single MTP is isolated (Cosmid-Midipräp Kit, Qiagen, Langen, Germany). The PCR-analysis with the "nested primers" results in a DNA of MTP2 with the expected size. For identification of the coordinates of the positive clone on MTP2 in a second step the clones of the horizontal 24 rows are each pooled and analysed by means of colony PCR. By means of an inoculating wire loop a small amount of cell material is applied to the PCR incubation. PCR is performed using the nested primers RS1_F1 (SEQ ID NO:45) and Asb_030730_R (SEQ ID NO:46) under the conditions described below.

PCR Conditions:

| Cycles | Time   | Temperature |
|--------|--------|-------------|
| 1      | 15 min | 95° C.      |
|        | 30 sec | 95° C.      |
| 30     | 30 sec | 50° C.      |
|        | 30 sec | 72° C.      |
| 1      | 7 min  | 72° C.      |

After that, the clones of the positive rows 15 and 16 are screened one by one by means of colony PCR (see above). By this procedure, the clones of the coordinates H15 and H16 are identified as positive. The cosmid DNA of these clones is isolated subsequently and used for sequencing.

E) Identification of a Gene Coding for a secADH out of *R. ruber* DSM 14855

Analysis is performed using cosmid DNA isolated from the positive cosmid-clone (Ex1_M2_H16) identified by the above described Grid-PCR-Screening. For sequencing of this cosmid clone an ABI 310 Genetic Analyzer and ABI Big Dye Terminator V 1.1 chemistry is used according to the instructions provided by the manufacturer. Hereby, an open-reading-frame (ORF) of 1038 bp is identified (SEQ ID NO: 47, see below) that, in spite of the difficulties in obtaining the final sequence, shows similarity but not identity to known alcohol dehydrogenases. Furthermore, the deduced 346 aminoacid-sequence (SEQ ID NO: 48, see below) matches perfectly with the partial aa-sequences of the native enzyme isolated out of *R. ruber* DSM 14855.

Nucleotide Sequence of the DNA Coding for ADH-A from *Rhodococcus rubber* DSM 14855:

```
ATGAAAGCCGTCCAGTACACCGAGATCGGCTCCGAGCCGGTCGTTGTCGACATCCCCACCCCGACGCC    (SEQ ID NO: 47)

CGGGCCGGGTGAGATCCTGCTGAAGGTCACCGCGGCCGGGCTGTGCCACTCGGACATCTTCGTGATGG

ACATGCCGGCGGCGCAGTACGCCTACGGCCTGCCGCTCACCCTCGGCCACGAGGGTGTCGGCACCGTC

GCCGAACTCGGCGAGGGCGTCACGGGATTCGGGGTGGGGGACGCCGTCGCCGTGTACGGGCCGTGGGG

CTGCGGTGCGTGCCACGCCTGCGCGCGCGGCCGGGAGAACTACTGCACCCGCGCCGCCGACCTGGGCA

TCACGCCACCCGGTCTCGGCTCGCCCGGATCGATGGCCGAGTACATGATCGTCGATTCGGCGCGCCAC

CTCGTCCCGATCGGAGACCTCGACCCGGTCGCCGCGGCGCCGCTCACCGACGCCGGTCTGACGCCGTA

CCACGCGATCTCCCGGGTCCTGCCGCTGCTGGGGCCGGGCTCGACGGCCGTCGTCATCGGTGTCGGCG
```

-continued

```
GGCTCGGCCACGTCGGCATCCAGATCCTGCGCGCCGTCAGCGCGGCCCGTGTGATCGCCGTCGACCTC

GACGACGACCGTCTCGCCCTCGCCCGCGAGGTCGGCGCCGACGCGGCGGTGAAGTCGGGCGCCGGTGC

GGCGGACGCGATCCGGGAACTGACCGGCGGCCAGGGCGCGACGGCGGTGTTCGACTTCGTCGGCGCCC

AGTCGACGATCGACACGGCGCAGCAGGTGGTCGCGGTCGACGGGCACATCTCGGTCGTGGGCATCCAC

GCCGGCGCACACGCCAAGGTCGGGTTCTTCATGATCCCGTTCGGCGCCTCCGTCGTGACCCCGTACTG

GGGCACCCGGTCGGAACTGATGGAGGTCGTCGCGCTGGCCCGCGCCGGCCGGCTGGACATCCACACCG

AGACGTTCACCCTCGACGAGGGGCCGGCGGCGTACCGGCGGCTGCGCGAGGGCAGCATCCGCGGCCGC

GGCGTGGTGGTTCCCTGA
```

15

Peptide Sequence of ADH-A from *Rhodococcus rubber* DSM 14855:

```
MKAVQYTEIGSEPVVVDIPTPTPGPGEILLKVTAAGLCHSDIFVMDMPAAQYAYGLPLTLGHEGVGTV    (SEQ ID NO: 48)

AELGEGVTGFGVGDAVAVYGPWGCGACHACARGRENYCTRAADLGITPPGLGSPGSMAEYMIVDSARH

LVPIGDLDPVAAAPLTDAGLTPYHAISRVLPLLGPGSTAVVIGVGGLGHVGIQILRAVSAARVIAVDL

DDDRLALAREVGADAAVKSGAGAADAIRELTGGQGATAVFDFVGAQSTIDTAQQVVAVDGHISVVGIH

AGAHAKVGFFMIPFGASVVTPYWGTRSELMEVVALARAGRLDIHTETFTLDEGPAAYRRLREGSIRGR

GVVVP
```

30

Thus in spite of the difficulties described, the sequences responsible for the ADH-A activity can be obtained both on the polynucleotide as well as peptide level.

Deposition and Characteristics of the Microorganism

The following microorganism has been deposited on Mar. 4, 2002, according to the Budapest Treaty with the DSMZ—Deutsche Sammlung von Mikroorganismen und Zellkulturen GmbH, Mascheroder Weg 1b, D-38124 Braunschweig under the number DSM 14855:

*Rhodococcus ruber* DSM 44541 (now *Rhodococcus ruber* DSM 14855).

The strain has the following properties:
Colour RAL: 3012-3022 (salmon pink).
Morphology: elementary ramification rod/coccus growth cycle.
Biochemical properties: fatty acids: 5-30% 16:0; 5-15% 16:1; 5-15% 18:0; 15-30% 18:1; 15-30% 18-Me. Mycolic acid $C_{42-50}$.
Possesses epoxide-hydrolase, nitrilase and ester-hydrolase activities.

*Rhodococcus ruber* DSM 14855 is isolated from the lower Rhine on hexane as sole carbon source.

The strains can be kept on a complex culture medium as described above at 30° C. and 130 rpm in L-shaking flasks with flow spoiler. After centrifugation, the pellet can be taken up in Tris-HCl buffer (pH 7.5, 50 mM), shock-frozen in liquid nitrogen and lyophilised, where desired and appropriate.

The invention claimed is:

1. An isolated polypeptide having alcohol dehydrogenase activity, comprising the amino acid sequence of SEQ ID No. 48, or a variant of said sequence having up to about 5% of the amino acids in the sequence of SEQ ID No. 48 replaced by different amino acids.

2. An isolated polypeptide having alcohol dehydrogenase activity, comprising the amino acid sequence of SEQ ID No. 48.

* * * * *